US011484753B2

(12) United States Patent
Nakashima et al.

(10) Patent No.: US 11,484,753 B2
(45) Date of Patent: Nov. 1, 2022

(54) WALKING TRAINING SYSTEM, DISPLAY METHOD, AND DISPLAY PROGRAM

(71) Applicant: TOYOTA JIDOSHA KABUSHIKI KAISHA, Toyota (JP)

(72) Inventors: Issei Nakashima, Toyota (JP); Takuma Nakamura, Nisshin (JP); Taiga Matsumoto, Nagoya (JP); Eiichi Saitoh, Nagoya (JP); Akihiro Saito, Ota-ku (JP); Satoshi Hirano, Nagoya (JP); Shigeo Tanabe, Toyoake (JP); Takuma Il, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 356 days.

(21) Appl. No.: 16/875,422

(22) Filed: May 15, 2020

(65) Prior Publication Data
US 2020/0384312 A1 Dec. 10, 2020

(30) Foreign Application Priority Data

Jun. 7, 2019 (JP) .............................. JP2019-106944

(51) Int. Cl.
*A63B 24/00* (2006.01)
*A61B 5/11* (2006.01)
(Continued)

(52) U.S. Cl.
CPC .......... *A63B 24/0006* (2013.01); *A61B 5/112* (2013.01); *A61B 5/742* (2013.01); *A61H 3/008* (2013.01); *A63B 22/02* (2013.01); *G06V 40/25* (2022.01); *G16H 20/30* (2018.01); *A61H 2003/007* (2013.01); *A61H 2201/501* (2013.01); *A61H 2201/5043* (2013.01); *A63B 2024/0009* (2013.01); *A63B 2024/0015* (2013.01)

(58) Field of Classification Search
CPC .... A63B 24/0006; A63B 22/02; G16H 20/30; G06V 40/25; A61B 5/112; A61B 5/742; A61H 3/008
See application file for complete search history.

(56) References Cited

U.S. PATENT DOCUMENTS

2017/0258370 A1* 9/2017 Plotnik-Peleg ........ A61B 5/744

FOREIGN PATENT DOCUMENTS

JP 2015-104397 A 6/2015

* cited by examiner

*Primary Examiner* — Curtis B Odom
(74) *Attorney, Agent, or Firm* — Oliff PLC

(57) ABSTRACT

The walking training system includes: a treadmill; a determination unit configured to determine whether a walking of the trainee on the treadmill is an abnormal walking based on predetermined abnormal walking symptoms; a display unit configured to display a result of a determination of each of the abnormal walking symptoms; a reception unit configured receive a selection of at least one result of the determination from the results of the determinations, each of which displayed on the display unit, in which regarding pieces of advice about adjustment items for improving the abnormal walking symptoms in the result of the determination which the reception unit has received the selection, the display unit preferentially displays the pieces of advice that are common to pieces of advice about adjustment items for improving the abnormal walking symptoms in a result of another determination in which the determination unit determines the abnormal walking.

7 Claims, 15 Drawing Sheets

(51) Int. Cl.
*A63B 22/02* (2006.01)
*A61B 5/00* (2006.01)
*G06V 40/20* (2022.01)
*A61H 3/00* (2006.01)
*G16H 20/30* (2018.01)

| SYMPTOMS | LEANING-BACKWARD OF BODY TRUNK | EXCESSIVE BENDING OF KNEE JOINT | PELVIC RETRACTION | DIFFICULTY IN SWINGING | RAPID EXTENSION OF KNEE JOINT |
|---|---|---|---|---|---|
| METHOD FOR IMPROVING SYMPTOMS | LIMITATION OF PLANTAR FLEXION: TO DORSIFLEXION | LIMITATION OF DORSIFLEXION: TO PLANTAR FLEXION | LIMITATION OF PLANTAR FLEXION: TO DORSIFLEXION | LIMITATION OF PLANTAR FLEXION: TO DORSIFLEXION | LIMITATION OF PLANTAR FLEXION: TO DORSIFLEXION |
| | SUPPLEMENTARY HEIGHT: INCREASE | ASSISTANCE FOR EXTENSION OF KNEE: INCREASE | LIMITATION OF DORSIFLEXION: TO DORSIFLEXION | SUPPLEMENTARY HEIGHT: INCREASE | ASSISTANCE FOR EXTENSION OF KNEE: INCREASE |
| | ASSISTANCE FOR SWINGING: INCREASE | ASSISTANCE FOR SWINGING: INCREASE | AMOUNT OF NON-WEIGHT BEARING: INCREASE | SUPPLEMENTARY HEIGHT: INCREASE | |
| | ADJUSTMENT OF SWINGING FORWARD OR BACKWARD: FORWARD | ADJUSTMENT OF SWINGING FORWARD OR BACKWARD: BACKWARD | ASSISTANCE FOR EXTENSION OF KNEE: INCREASE | ADJUSTMENT OF SWINGING FORWARD OR BACKWARD: FORWARD | |
| | BENDING ANGLE OF KNEE: INCREASE | FOOT FB: FOOTPRINT | ASSISTANCE FOR SWINGING: REDUCE | BENDING ANGLE OF KNEE: INCREASE | |
| | LOAD THRESHOLD: LOW | | ADJUSTMENT OF SWINGING FORWARD OR BACKWARD: BACKWARD | LOAD THRESHOLD: LOW | |
| | HANDRAIL: LOW | | FOOT FB: FOOTPRINT | LENGTH OF TIME OF STRETCHING KNEE: REDUCE | |
| | FRONTAL PLANE FB: REFERENCE LINE/FAN SHAPE | | NON-WEIGHT-BEARING POSITION OF LEG: OUTSIDE | LENGTH OF TIME OF STRETCHING KNEE: INCREASE | |
| | | | | HANDRAIL: LOW | |
| | | | | FRONTAL PLANE FB: REFERENCE LINE/FAN SHAPE | |

Fig. 9

| PELVIC RETRACTION | NUMBER OF OVERLAPS WITH OTHER SYMPTOMS | DISPLAY ORDER | CONFLICT WITH OTHER IMPROVEMENT METHODS |
|---|---|---|---|
| LIMITATION OF PLANTAR FLEXION: TO DORSIFLEXION | 4 | 1 | NO |
| LIMITATION OF DORSIFLEXION: TO DORSIFLEXION | 1 | 5 | YES |
| AMOUNT OF NON-WEIGHT BEARING: INCREASE | 1 | 6 | NO |
| ASSISTANCE FOR EXTENSION OF KNEE: INCREASE | 3 | 2 | NO |
| ASSISTANCE FOR SWINGING: REDUCE | 1 | 7 | YES |
| ADJUSTMENT OF SWINGING FORWARD OR BACKWARD: BACKWARD | 2 | 3 | YES |
| FOOT FB: FOOTPRINT | 2 | 4 | NO |
| NON-WEIGHT-BEARING POSITION OF LEG: OUTSIDE | 1 | 8 | NO |

Fig. 10

WALKING TRAINING SYSTEM, DISPLAY METHOD, AND DISPLAY PROGRAM

CROSS REFERENCE TO RELATED APPLICATIONS

This application is based upon and claims the benefit of priority from Japanese patent application No. 2019-106944, filed on Jun. 7, 2019, the disclosure of which is incorporated herein in its entirety by reference.

BACKGROUND

The present disclosure relates to a walking training system, a display method, and a display program.

A technique for measuring and evaluating a motion during walking training and displaying the result on a display unit is known (e.g., see Unexamined Patent Application Publication No. 2015-104397).

SUMMARY

When a trainee suffering from paralysis in a leg does walking training, several symptoms, which can be used to determine that the walking of the trainee is an abnormal walking, have already been known. A walking training system includes many adjustment items that can be adjusted to improve those symptoms. If some abnormal walking symptoms have been found in the walking of a trainee during training attempts, an assistant who assists walking training often cannot determine which and how adjustment items should be adjusted to effectively improve the abnormal walking symptoms of the trainee.

The present disclosure has been made to solve the above-described problem, and an object thereof is to provide a walking training system or the like for effectively improving abnormal walking symptoms of a trainee.

A first exemplary aspect is a walking training system, including:
  a treadmill that urges a trainee to walk;
  a determination unit configured to determine whether a walking of the trainee who walks on the treadmill is an abnormal walking based on a plurality of predetermined abnormal walking symptoms;
  a display unit configured to display a result of a determination of each of the plurality of abnormal walking symptoms by the determination unit;
  a reception unit configured receive a selection of at least one result of the determination from the results of the determinations, each of which is displayed on the display unit, in which
  regarding pieces of advice about adjustment items for improving the abnormal walking symptoms in the result of the determination which the reception unit has received the selection, the display unit preferentially displays the pieces of advice that are common to pieces of advice about adjustment items for improving the abnormal walking symptoms in a result of another determination in which the determination unit determines the abnormal walking.

If the display unit displays advice as described above, an assistant can immediately and appropriately recognize which and how adjustment items, which have a complicated relationship with each other, should be adjusted to effectively improve the abnormal walking symptom of a trainee who the assistant is assisting.

In the aforementioned walking training system, the display unit may change a display mode of each of the pieces of advice while taking a past display history into consideration. By changing the display mode of each of the pieces of advice while the display history is taken into consideration, it is possible to prevent only a specific abnormal walking symptom from being improved. Further, the display unit may change the display mode of each of the pieces of advice based on a degree of importance set in advance for each adjustment item. The adjustment items vary from those that can be expected to greatly improve abnormal walking symptoms to those that only somewhat provide notice to trainees, and accordingly it is possible to notify the assistant of more effective adjustment items by changing the display mode as described above.

Further, the reception unit may receive a selection of at least one piece of advice from the pieces of advice, each of which is displayed on the display unit, and the display unit may change the display mode of the result of the determination corresponding to the abnormal walking symptom with which the same piece of advice as the piece of advice received by the reception unit is associated. If the assistant can know which of a plurality of pieces of displayed advice is involved in improvement of the abnormal walking symptoms as described above, he/she can adjust the adjustment items that are effective for attaining the improvement goal set for the trainee.

Further, the reception unit may receive a selection of at least one piece of advice from the pieces of advice, each of which is displayed on the display unit, and the display unit may change the display mode of the result of the determination corresponding to the abnormal walking symptom with which piece of advice that conflicts with the piece of advice received by the reception unit is associated. An adjustment to improve a certain abnormal walking symptom may conflict with an adjustment to improve other abnormal walking symptoms. As the assistant can adjust the adjustment items in accordance with the abnormal walking symptoms of the trainee due to having knowledge of such conflict, it is easy to avoid making specific abnormal walking symptoms worse.

A second exemplary aspect is a display method for displaying, on a display unit, pieces of advice about a walking determined to be an abnormal walking in a walking training system including a treadmill that urges a trainee to walk and the display unit, the display method including:
  a determination step of determining whether a walking of the trainee who walks on the treadmill is an abnormal walking based on a plurality of predetermined abnormal walking symptoms;
  a first display step of displaying, on the display unit, a result of a determination of each of the plurality of abnormal walking symptoms by the determination step;
  a reception step of receiving a selection of at least one result of the determination from the results of the determinations, each of which is displayed on the display unit; and
  a second display step of displaying pieces of advice about adjustment items for improving the abnormal walking symptoms in the result of the determination which the selection has received in the reception step, in which
    in the second display step, the pieces of advice that are common to pieces of advice about adjustment items for improving the abnormal walking symptoms in a result of another determination in which the abnormal walking is determined are preferentially displayed.

A third exemplary aspect is a display program for displaying, on a display unit, pieces of advice about a walking determined to be an abnormal walking in a walking training system including a treadmill that urges a trainee to walk and the display unit, the display program causing a computer to execute:

a determination step of determining whether a walking of the trainee who walks on the treadmill is an abnormal walking based on a plurality of predetermined abnormal walking symptoms;

a first display step of displaying, on the display unit, a result of a determination of each of the plurality of abnormal walking symptoms by the determination step;

a reception step of receiving a selection of at least one result of the determination from the results of the determinations, each of which is displayed on the display unit; and a second display step of displaying pieces of advice about adjustment items for improving the abnormal walking symptoms in the result of the determination which the selection has received in the reception step, in which in the second display step, the pieces of advice that are common to pieces of advice about adjustment items for improving the abnormal walking symptoms in a result of another determination in which the abnormal walking is determined are preferentially displayed.

Even in the above second and third aspects, as in the case of the first aspect, an assistant can appropriately and immediately recognize which and how adjustment items, which have a complicated relationship with each other, should be adjusted to effectively improve the abnormal walking symptom of a trainee who the assistant is assisting.

According to the present disclosure, it is possible to provide a walking training system or the like for effectively improving abnormal walking symptoms of a trainee.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 9 is a diagram showing a list of the detected abnormal walking symptoms and a method for improving the symptoms;

FIG. 10 is a diagram showing processing done until a display mode of the improvement method is determined;

DESCRIPTION OF EMBODIMENTS

Hereinafter, although the present disclosure will be described with reference to an embodiment of the present disclosure, the present disclosure according to claims is not limited to the following embodiment. Moreover, all the components described in the following embodiment are not necessarily essential for means for solving problems.

Figure 1:
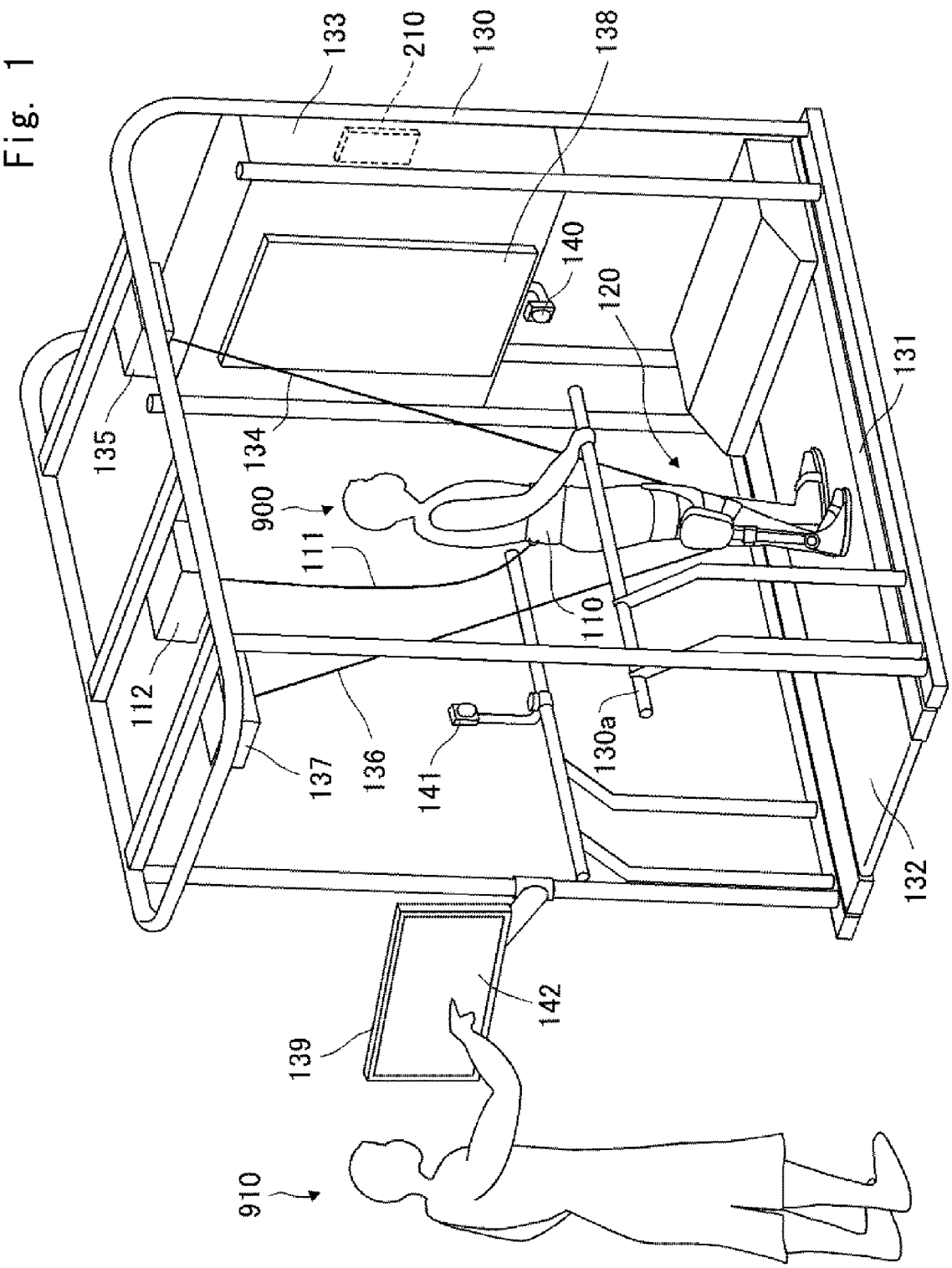
FIG. 1 is a schematic perspective view of a walking training apparatus according to an embodiment.

FIG. 1 is a schematic perspective view of a walking training apparatus 100 according to this embodiment. The walking training apparatus 100 is an example of a walking training system and is an apparatus by which a trainee 900, who is a hemiplegia patient suffering from paralysis in one of his/her legs, does walking training. The walking training apparatus 100 mainly includes a control panel 133 attached to a frame 130 forming an overall framework, a treadmill 131 on which the trainee 900 walks, and a walking assistance apparatus 120 attached to the diseased leg, which is the leg on the paralyzed side of the trainee 900.

The frame 130 is disposed on the treadmill 131 mounted on a floor surface in a standing state. The treadmill 131 rotates a ring-shaped belt 132 by using a motor (not shown). The treadmill 131 is an apparatus which urges the trainee 900 to walk. The trainee 900, who does walking training, gets on the belt 132 and tries to walk in accordance with the movement of the belt 132.

The frame 130 supports, for example, the control panel 133 housing an overall control unit 210 that controls motors or sensors, and a training monitor 138 that is formed by, for example, a liquid-crystal panel and presents the progress of the training and the evaluation comment to the trainee 900. The training monitor 138 is installed so that the trainee 900 can visually recognize it while he/she is walking on the belt 132 of the treadmill 131. Further, the frame 130 supports a front pulling unit 135 in a position located above and in front of the head of the trainee 900, a harness pulling unit 112 in a position located above the head of the trainee 900, and a rear pulling unit 137 in a position located above and behind the head of the trainee 900. Further, the frame 130 includes a handrail 130a for the trainee 900 to grasp.

A front camera unit 140 takes an image of the trainee 900 at an angle of view at which the gait of the trainee 900 can be recognized from the front. A side camera unit 141 takes an image of the trainee 900 at an angle of view at which the gait of the trainee 900 can be recognized from the side. Each of the front camera unit 140 and the side camera unit 141 includes a set of a lens and an image pickup device having an angle of view that the whole body including the head of the trainee 900 who is standing on the belt 132 can be captured. The image pickup device is, for example, a CMOS image sensor, and it converts an optical image formed on an image forming surface into an image signal. The front camera unit 140 is installed near the training monitor 138 so that it faces the trainee 900. The side camera unit 141 is installed on the handrail 130a so that it captures the trainee 900 from the side.

One end of a front wire 134 is coupled to a winding mechanism of the front pulling unit 135 and the other end of the front wire 134 is connected to the walking assistance apparatus 120. The winding mechanism of the front pulling unit 135 winds up and pays out the front wire 134 in accordance with the movement of the diseased leg by turning on or off the motor (not shown). Similarly, one end of a rear wire 136 is coupled to a winding mechanism of the rear pulling unit 137 and the other end of the rear wire 136 is coupled to the walking assistance apparatus 120. The winding mechanism of the rear pulling unit 137 winds up and pays out the rear wire 136 in accordance with the movement of the diseased leg by turning on or off the motor (not shown). By such cooperative operations performed by the front and the rear pulling units 135 and 137, the load (e.g., the weight) of the walking assistance apparatus 120 is cancelled out so that it does not act as a burden on the diseased leg, and a swinging motion of the diseased leg is assisted in accordance with a set level.

An operator 910 who is a training assistant sets an assisting level to a high value for a trainee having severe paralysis. The operator 910 is a physical therapist or a medical doctor who has authority to make a selection, a modification, or an addition to the setting items of the walking training apparatus 100. When the assisting level is adjusted to a large value, the front pulling unit 135 winds up the front wire 134 with a relatively strong force in synchronization with the swinging motion of the diseased leg. When the assistance becomes unnecessary as the training proceeds, the operator adjusts the assisting level to a minimum value. When the assisting level is adjusted to the minimum value, the front pulling unit 135 winds up the front wire 134, in synchronization with the swinging motion of the diseased leg, with a force enough to cancel the weight of the walking assistance apparatus 120.

The walking training apparatus 100 includes a safety apparatus mainly including a safety harness 110, a harness wire 111, and the harness pulling unit 112. The safety harness 110 is a belt wrapped around the abdomen of the trainee 900 and is fixed to the waist by, for example, a hook-and-loop fastener. One end of the harness wire 111 is coupled to the safety harness 110, and the other end thereof is coupled to a winding mechanism of the harness pulling unit 112. The winding mechanism of the harness pulling unit 112 winds up and pays out the harness wire 111 by turning on or off the motor (not shown). By such a configuration, when the trainee 900 greatly loses his/her balance, the safety apparatus winds up the harness wire 111 in accordance with the instruction from the overall control unit 210 that has detected the movement of the trainee 900 and supports the upper body of the trainee 900 with the safety harness 110.

A management monitor 139 is attached to the frame 130 and is a display apparatus for the operator 910 to perform monitoring and operation. The management monitor 139 is, for example, a liquid crystal panel, and includes a touch panel 142 superimposed on the surface thereof. The management monitor 139 presents various menu items related to the training setting, various parameter values at the time of training, the result of a determination of an abnormal walking symptom, and the like. Further, the operator 910 makes a selection, a modification, or an addition to the setting items via the touch panel 142 or a mouse (not shown).

Figure 2:
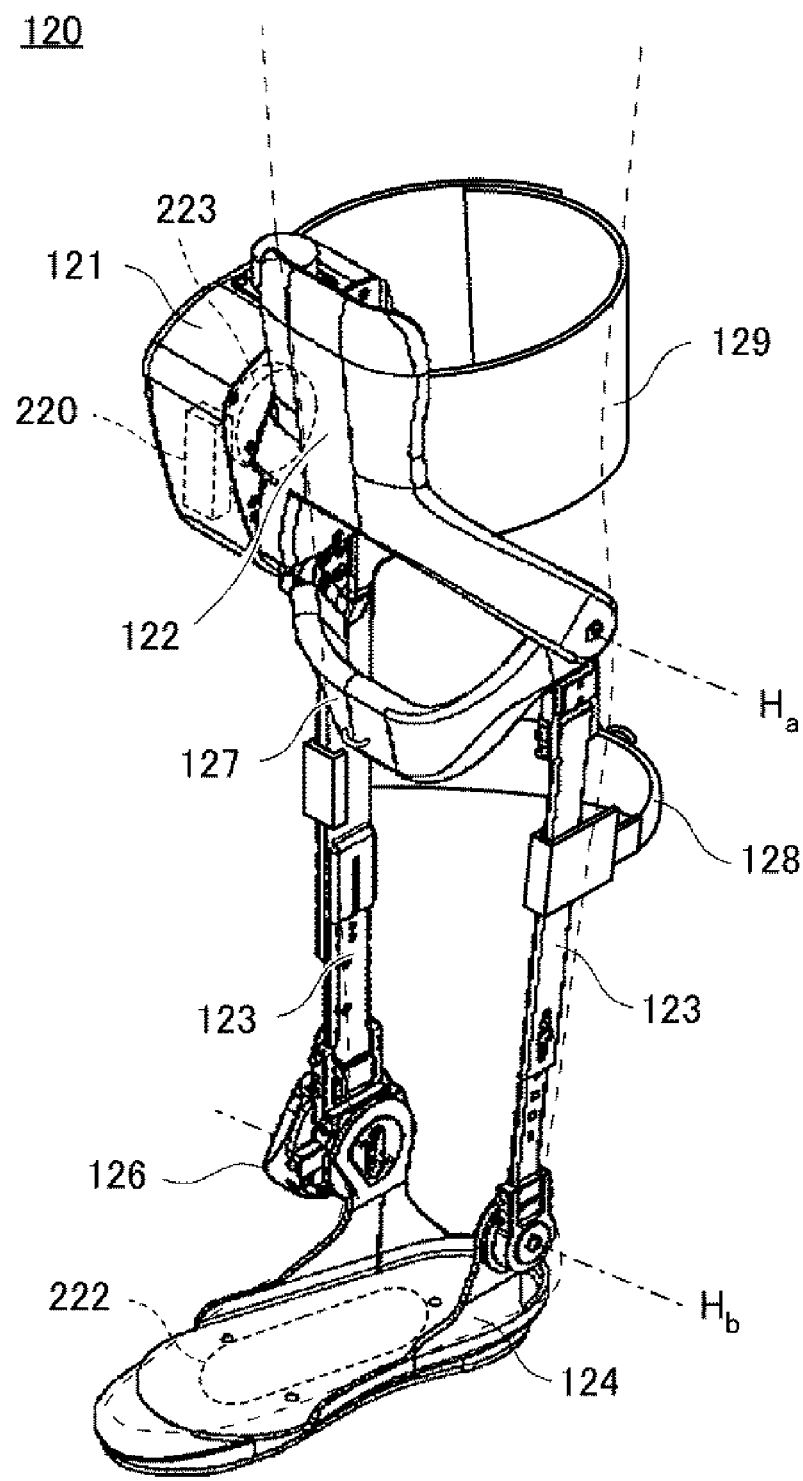
FIG. 2 is a schematic perspective view of a walking assistance apparatus.

The walking assistance apparatus 120 is attached to the diseased leg of the trainee 900 to assist the trainee 900 in his/her walking by reducing the burden of extending and bending motions in the knee joint of the diseased leg. FIG. 2 is a schematic perspective view of the walking assistance apparatus 120. The walking assistance apparatus 120 mainly includes a control box 121, a plurality of frames that support each part of the diseased leg, and a load sensor 222 for detecting a load applied to the sole of the trainee 900.

The control box 121 includes an auxiliary control unit 220 that controls the walking assistance apparatus 120, and further includes a motor (not shown) that generates a driving force for assisting the extending and the bending motions of the knee joint. The frames that support each part of the diseased leg include an upper leg frame 122, lower leg frames 123 rotatably coupled to the upper leg frame 122, a sole frame 124 rotatably coupled to the lower leg frame 123, a front coupling frame 127 for coupling the front wire 134, and a rear coupling frame 128 for coupling the rear wire 136. The front coupling frame 127 is provided so that it extends in the horizontal direction of the upper leg on the front side thereof and connects to the upper leg frame 122 at both ends. The rear coupling frame 128 is provided so that it extends in the horizontal direction of the lower leg on the rear side thereof, and connects, at both ends, to the lower leg frames 123, each of which extends vertically.

The upper leg frame 122 and the lower leg frame 123 relatively rotate around a hinge axis $H_a$ shown in FIG. 2. The motor of the control box 121 rotates in accordance with an instruction from the auxiliary control unit 220 to assist the upper leg frame 122 and the lower leg frame 123 so that they relatively open and close around the hinge axis $H_a$. An angle sensor 223 housed in the control box 121 is, for example, a rotary encoder, and detects an angle formed between the upper leg frame 122 and the lower leg frame 123 around the hinge axis $H_a$. The lower leg frame 123 and the sole frame 124 relatively rotate around a hinge axis $H_b$ shown in FIG. 2. A range of the angle in which they relatively rotate is adjusted in advance by an adjustment mechanism 126.

The upper leg frame 122 includes an upper leg belt 129. The upper leg belt 129 is a belt provided integrally with the upper leg frame and is wound around the upper leg of the diseased leg to fix the upper leg frame 122 to the upper leg. This structure prevents the entire walking assistance apparatus 120 from shifting with respect to the leg of the trainee 900.

The load sensor 222 is a load sensor embedded in the sole frame 124. The load sensor 222 detects the magnitude and the distribution of a vertical load applied to the sole of the trainee 900. The load sensor 222 is, for example, a load detection sheet of a resistance change detection type including electrodes arranged in a matrix.

Figure 3:
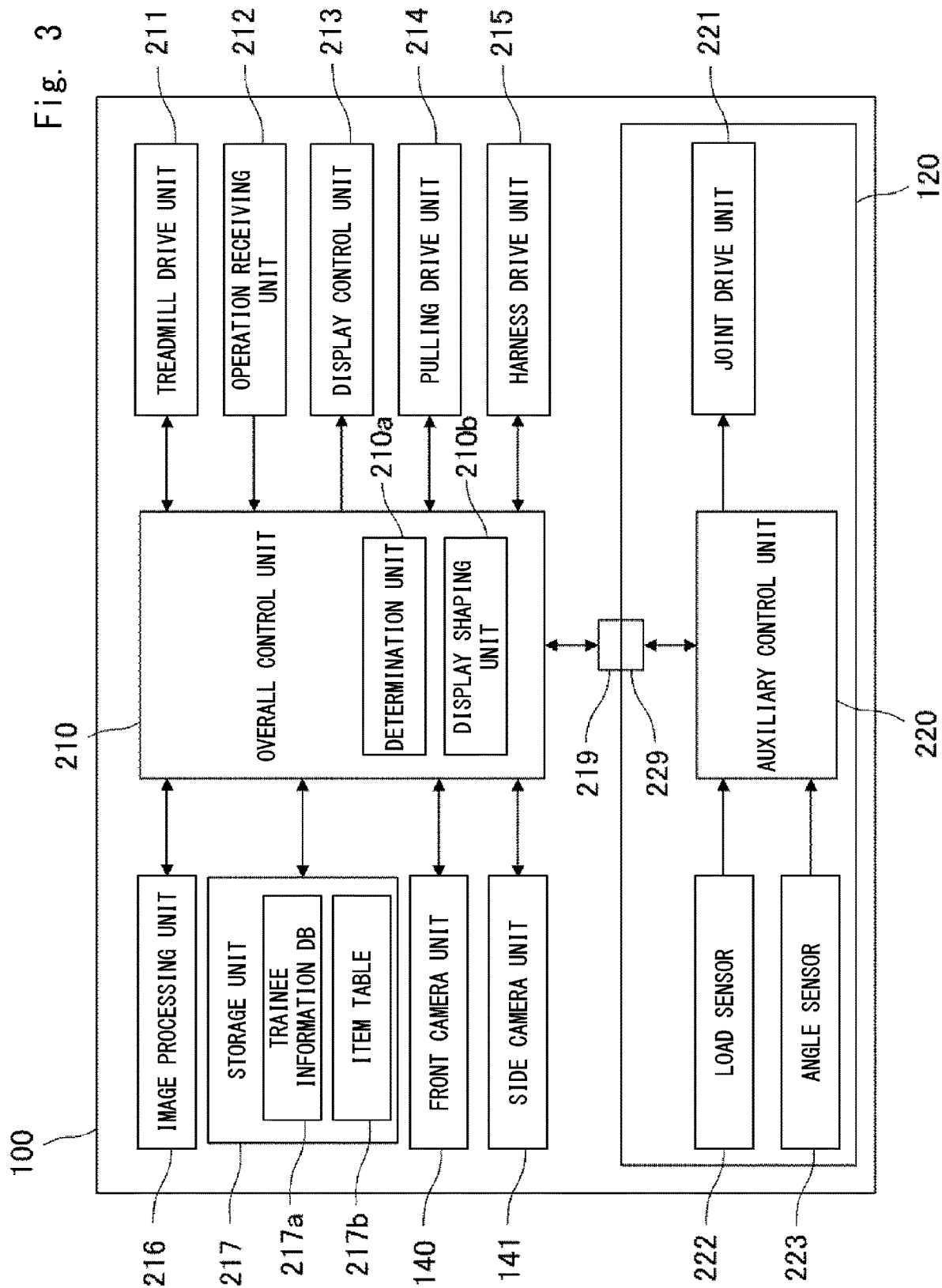
FIG. 3 is a diagram showing a system configuration of the walking training apparatus.

Next, a system configuration of the walking training apparatus 100 is described. FIG. 3 is a diagram showing the system configuration of the walking training apparatus 100. The overall control unit 210 is, for example, an MPU, and controls the overall operation of the apparatus by executing a control program loaded from a storage unit 217. A treadmill drive unit 211 includes a motor for rotating the belt 132 and a drive circuit for the motor. The overall control unit 210 controls the rotation of the belt 132 by sending a drive signal to the treadmill drive unit 211. For example, the rotation speed of the belt 132 is adjusted in accordance with a set training level.

An operation reception unit 212 includes various input devices that receive an input operation from the trainee 900 or the operator 910 and transmit an operation signal to the overall control unit 210. The touch panel 142 is one of the input devices included in the operation reception unit 212. The trainee 900 or the operator 910 operates the operation buttons and the touch panel, the accompanying remote controller, or the like, which constitutes the operation reception unit 212, and thereby providing an instruction to turn on/off a power supply or to start a training, entering numerical values for the setting, and selecting a menu item. The operation reception unit 212 may include a voice interaction apparatus or an image recognition apparatus. A display control unit 213 generates a display video image in accordance with a control signal from a display shaping unit 210b of the overall control unit 210 and displays the display image on the training monitor 138 or the management monitor 139.

A pulling drive unit 214 includes a motor for pulling the front wire 134 and a drive circuit for the motor, and a motor for pulling the rear wire 136 and a drive circuit for the motor. The overall control unit 210 controls the winding of each of the front wire 134 and the rear wire 136 by sending a drive signal to the pulling drive unit 214. Further, the overall control unit 210 controls the pulling force of each wire not only by a winding operation but also by controlling the drive torques of the motors. The overall control unit 210 identifies (i.e., determines), for example, the timing at which the diseased leg is changed from a leg-standing state to a leg-idling state from the result of the detection performed by the load sensor 222, and increases or reduces the pulling force of each wire in synchronization with that timing, thereby assisting the swinging motion of the diseased leg.

A harness drive unit 215 includes a motor for pulling the harness wire 111 and a drive circuit for the motor. The overall control unit 210 controls the winding of the harness wire 111 and the pulling force the harness wire 111 by sending a drive signal to the harness drive unit 215. For example, when the trainee 900 greatly loses his/her balance, the overall control unit 210 winds the harness wire 111 by a fixed amount to prevent the trainee from falling.

An image processing unit 216 generates image data by performing image processing on the image signals received from the front camera unit 140 and the side camera unit 141 in accordance with the control signal received from the overall control unit 210. Further, the image processing unit 216 can perform a specific image analysis by performing image processing on the image signals received from the front camera unit 140 and the side camera unit 141 in accordance with the instruction received from the overall control unit 210. For example, it is possible to detect the positions of the shoulders and the hip joint of the trainee from information such as extracted edges. Such positional information serves as basic information for evaluating the state of the body trunk, the legs, and the soles of the trainee 900 during movement of the leg.

The storage unit 217 is a nonvolatile storage medium, and for example, a solid state drive is used. The storage unit 217 stores, in addition to a control program for controlling the walking training apparatus 100 and a display program for displaying the result of a determination of an abnormal walking and advice for the abnormal walking, various parameter values, functions, lookup tables and the like which are used for the control and the calculation. In particular, the storage unit 217 stores a trainee information DB 217a, which is a database in which individual information about trainees who uses the walking training apparatus 100 is accumulated, and an item table 217b, which is a reference table that summarizes a plurality of abnormal walking symptoms and pieces of advice about adjustment items corresponding to the respective symptoms. Note that these databases may be stored, for example, in a storage device connected to a network, and in that case, the walking training apparatus 100 acquires required individual information pieces and reference tables from the storage device as necessary from these databases.

The front camera unit 140 and the side camera unit 141 repeat an image pickup operation in accordance with a control signal received from the overall control unit 210 and output an image signal to the image processing unit 216. Further, the overall control unit 210 functions as a function execution unit that performs various calculations and controls. A determination unit 210a determines whether the walking of the trainee 900 who walks on the treadmill 131 is an abnormal walking based on a plurality of predetermined abnormal walking symptoms. Specifically, the determination unit 210a determines whether the result of the determination corresponds to each of the abnormal walking symptoms using the result of the analysis performed by the image processing unit 216, the result of the output from the load sensor 222, and the like. The display shaping unit 210b selects information to be presented via the training monitor 138 and the management monitor 139, adjusts the display format, and generates a display video image. The generated display video image is displayed on the training monitor 138 or the management monitor 139 via the display control unit 213.

As described above, the walking assistance apparatus 120 is attached to the diseased leg of the trainee 900. Further, the walking training apparatus 100 includes a communication connecting IF 219 connected to the overall control unit 210 in order to provide an instruction to the walking assistance apparatus 120, receive sensor information therefrom, and so on. Similarly, the walking assistance apparatus 120 is provided with a communication connecting IF 229 which is connected to the communication connecting IF 219 wirelessly or through a wire. The communication connecting IF 229 is connected to the auxiliary control unit 220 of the walking assistance apparatus 120. The communication connecting IFs 219 and 229 are communication interfaces in conformity with communication standards such as a wireless LAN.

The auxiliary control unit 220 is, for example, an MPU, and controls the walking assistance apparatus 120 by executing a control program provided from the overall control unit 210. Further, the auxiliary control unit 220 notifies the overall control unit 210 of a state of the walking assistance apparatus 120 via the communication connecting IFs 219 and 229. Further, the auxiliary control unit 220, for example, starts or stops the walking assistance apparatus 120 in response to an instruction from the overall control unit 210.

A joint drive unit 221 includes a motor of the control box 121 and a drive circuit for the motor. The auxiliary control unit 220 assists the upper leg frame 122 and the lower leg frame 123 by sending a drive signal to the joint drive unit 221 so that the upper leg frame 122 and the lower leg frame 123 relatively open and close around a hinge axis $H_a$. Such movements assist extending and bending motions of the knee, prevent the knee from accidentally bending, and so on. The load sensor 222 detects the magnitude and the distribution of the vertical load applied to the sole of the trainee 900 as described above and transmits a detection signal to the auxiliary control unit 220.

The angle sensor 223 detects an angle formed between the upper leg frame 122 and the lower leg frame 123 around the hinge axis $H_a$ as described above and transmits a detection signal to the auxiliary control unit 220. The auxiliary control unit 220 receives the detection signal and calculates an opening angle of the knee joint. The auxiliary control unit 220 transmits the detection signal received from the load sensor 222 and the detection signal received from the angle sensor 223 to the determination unit 210a. The auxiliary control unit 220 may transmit, to the determination unit

210a, the results of the determination whether the leg is in a leg-idling or a leg-standing state and the estimation of a switching timing between a leg-standing state and a leg-idling state, which are obtained by analyzing the aforementioned detection signals.

An example of the determination method performed by the determination unit 210a is further described below. The determination unit 210a calculates the inclination of the body trunk of the trainee 900 who is walking from the result of the analysis, which is performed by the image processing unit 216, of the trainee image taken by the front camera unit 140 and the side camera unit 141. Specifically, the determination unit 210a determines the inclination of the body trunk in the image by connecting the reference positions of the main skeletal frame such as the positions of the shoulders and the hip joint analyzed by the image processing unit 216 to each other, and calculates the angle formed by the direction in which the body trunk extends and the vertical axis of the walking surface as an inclination angle. The determination unit 210a determines whether the walking of the trainee 900 is abnormal using the calculated inclination of the body trunk. The determination unit 210a also uses, for example, an image analysis performed by the image processing unit 216, a dragging and a stumbling of the leg when the trainee 900 is walking detected from the sensor output of the load sensor 222 and the like, and a grasping of the handrail 130a as subjects to be considered to determine whether the walking of the trainee 900 is abnormal.

Whether or not the walking is abnormal can be determined, for example, based on the following six criteria. A first criterion is whether the distance in the walking direction from the hip joint to the ankle joint when the diseased leg lands on the ground after a leg-idling period is equal to or greater than a reference value. If it is less than the reference value, it is assumed that the diseased leg cannot be sufficiently swung, and thus it is determined that the abnormal walking symptom has appeared. This abnormal walking symptom is referred to as "pelvic retraction". A second criterion is whether the bending angle of the knee joint during the period when the diseased leg is in a leg-standing state is equal to or larger than a reference angle. If it is equal to or larger than the reference angle, it is assumed that the weight of the upper body is concentrated on the knee joint, and thus it is determined that the abnormal walking symptom has appeared. This abnormal walking symptom is referred to as "excessive bending of the knee joint".

A third criterion is whether the distance in the walking direction from the hip joint to the ankle joint at the time of swinging when the diseased leg switches from a leg-standing period to a leg-idling period is equal to or greater than a reference value. If it is less than the reference value, it is assumed that the weight of the upper body cannot be freely shifted, and thus it is determined that the abnormal walking symptom has appeared. This abnormal walking symptom is referred to as "difficulty in swinging". A fourth criterion is whether the inclination angle of the body trunk in the front direction during the period when the diseased leg is in a leg-standing state is equal to or larger than a reference angle. If it is equal to or larger than the reference angle, it is assumed that the posture is one in which the body trunk is leaned forward, and thus it is determined that the abnormal walking symptom has appeared. This abnormal walking symptom is referred to as "leaning-forward of the body trunk".

A fifth criterion is whether the inclination angle of the body trunk toward the diseased leg during the period when the diseased leg is in a leg-standing state is equal to or larger than a reference angle. If it is equal to or larger than the reference angle, it is assumed that the movement in the horizontal direction is large, and thus it is determined that the abnormal walking symptom has appeared. This abnormal walking symptom is referred to as "excessive movement of the pelvis to the paralyzed side". A sixth criterion is whether the inclination angle of the body trunk in the front direction during the period when the diseased leg is in a leg-idling state is equal to or larger than a reference angle. If it is less than the reference angle, it is assumed that the weight of the upper body cannot be freely shifted and the body trunk is leaned backward, and thus it is determined that the abnormal walking symptom has appeared. This abnormal walking symptom is referred to as "leaning-backward of the body trunk".

The above-described six abnormal walking symptoms are each specific abnormal walking symptoms that may lead to a fall depending on a degree of the detected distance in the walking direction from the hip joint to the ankle joint or a degree of the detected bending angle of the knee joint and inclination angle of the body trunk. In the measurement range of a measurement target in each specific abnormal walking symptom, a first hierarchy (a KR hierarchy), which is a range where there is a possibility of falling, and a second hierarchy (a KP hierarchy), which is a range where there is no possibility of falling, are set. For example, the measurement target of "pelvic retraction" is the distance in the walking direction from the hip joint to the ankle joint as described above, and the range from 0 to less than $D_1$ is set as the KR hierarchy, the range from $D_1$ to less than $D_2$ is set as the KP hierarchy, and the range of $D_2$ or more is set as a normal hierarchy. It is determined that the walking is an abnormal walking that may lead to a fall if a detected distance D is included in the KR hierarchy, it is determined that the walking is an abnormal walking that may not lead to a fall if the detected distance D is included in the KP hierarchy, and it is determined that the walking is a normal walking if the detected distance D is included in the normal hierarchy. Each boundary value ($D_1$, $D_2$, etc.) is set in advance by a doctor or the like in accordance with the height, the weight, the degree of paralysis, and the like of the trainee 900. Note that although the aforementioned abnormal walking symptoms are determined as specific abnormal walking symptoms in this embodiment, the specific abnormal walking symptoms may be determined by focusing on other criteria that may lead to a fall.

The abnormal walking symptoms include, in addition to the specific abnormal walking symptoms that may lead to a fall, abnormal walking symptoms indicating a gait different from that of a healthy person although it does not lead to a fall. Such abnormal walking symptoms include "circumduction gait" in which the diseased leg is swung out, "pelvic elevation" in which the pelvis is elevated, and "medial whip" in which the heel is unnaturally elevated during a leg-idling state. The measurement range of the measurement target in each of the above-described abnormal walking symptoms is divided into two: the KP hierarchy and the normal hierarchy, and it is determined that the walking is abnormal if the result of the measurement is included in the KP hierarchy, and it is determined that the walking is normal if the result of the measurement is included in the normal hierarchy.

Figure 4A:
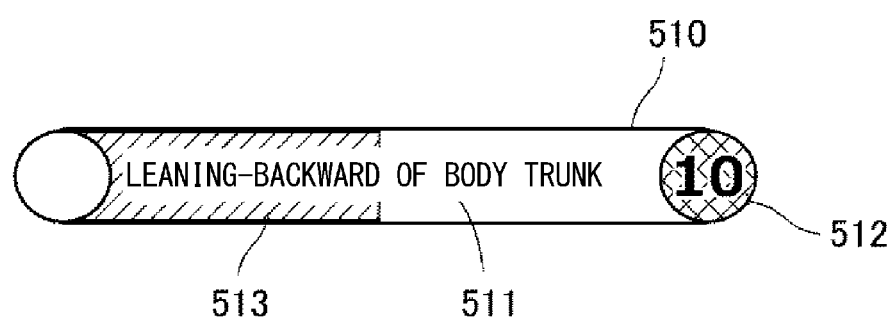
FIG. 4A is an example of a display object that displays a result of a determination of an abnormal walking symptom.
Figure 4B:
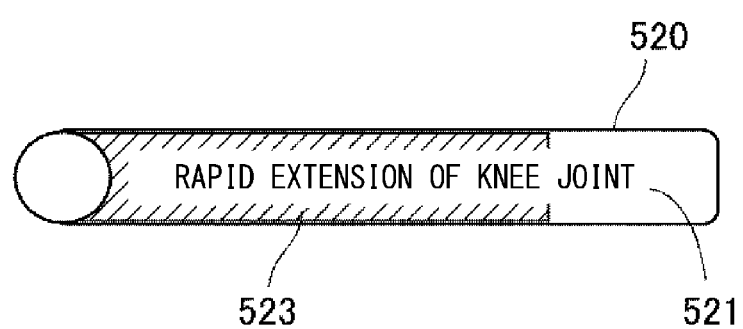
FIG. 4B is an example of a display object that displays a result of a determination of an abnormal walking symptom.

The determination unit 210a determines whether a walking is abnormal, for example, using the result of the analysis performed by the image processing unit 216 that is sequentially obtained during a training attempt, the detection signals received from the load sensor 222 and the angle sensor 223. The display shaping unit 210b shapes the result of the determination made by the determination unit 210a into a display object and displays the display object on the training monitor 138 and the management monitor 139. FIG. 4 is an example of the display object that visually indicates the result of the determination of the abnormal walking symptom. In particular, FIG. 4A is an example of a first object 510 indicating the result of the determination of the specific abnormal walking symptom, and FIG. 4B is an example of a second object 520 indicating the result of the determination of the abnormal walking symptom other than the specific abnormal walking symptom.

The first object 510 has an oval shape formed by connecting two circles arranged on the left and the right sides, respectively, of the object to each other with an external common tangent, and includes a symptom title 511, a KR index 512, and a SUM index 513. The symptom title 511 is character information indicating which result of the determination of the specific abnormal walking symptom is indicated by the first object 510. The example in FIG. 4A shows character information of "leaning-backward of the body trunk".

The KR index 512 is a numerical value indicating the number of times that the determination unit 210a has determined that the specific abnormal walking symptom ("leaning-backward of the body trunk" in this case) falls under the KR hierarchy among those symptoms determined by the determination unit 210a during a training attempt. The KR index 512 is provided inside the right circle of the first object 510. The example in FIG. 4A shows a numerical value of "10". The SUM index 513 is a bar graph extending from the left end of the first object 510 in accordance with the number of times that the determination unit 210a has determined the specific abnormal walking symptom during a training attempt (i.e., the number of times that the abnormal walking symptom falls under either KR hierarchy or the KP hierarchy). In the example shown in FIG. 4A, the bar graph is indicated by oblique lines extending to the vicinity of the center of the first object 510. Displaying the result of the determination of a specific abnormal walking symptom in such an integrated display mode enables the trainee 900 and the operator 910 to collectively, visually recognize the title of the specific abnormal walking symptom, the determined overall frequency, and the frequency in which an unsafe state that may lead to a fall has been determined. That is, it is possible to recognize the above intuitively and immediately.

The second object 520 has a shape formed by removing the right circle indicating the KR index 512 from the first object 510, and includes a symptom title 521, and a KP index 523. The symptom title 521 is character information indicating which result of the determination of the specific abnormal walking symptom is indicated by the second object 520. The example in FIG. 4B shows character information of "rapid extension of the knee joint".

The KP index 523 is a bar graph extending from the left end of the second object 520 in accordance with the number of times that the determination unit 210a has determined the specific abnormal walking symptom during a training attempt. In the example shown in FIG. 4B, the bar graph is indicated by oblique lines extending slightly to the right side of the second object 520 from the center thereof. Note that the second object 520 indicates a result of the determination of the abnormal walking symptom other than the specific abnormal walking symptom, and accordingly there is no KR hierarchy in the measurement range of the measurement target and the number of times that the result of the measurement falls under the KP hierarchy is the number of times that the abnormal walking symptom has been determined. Displaying the result of the determination of the abnormal walking symptom in such an integrated display mode and the KP index 523 in the same display mode as that of the SUM index 513 enables the trainee 900 and the operator 910 to compare and recognize the frequency of each symptom.

Note that in this embodiment, the frequency in which the result of the measurement falls under the KR hierarchy is indicated by a numerical value like the KR index 512, and the total frequency in which the result of the measurement falls under either the KR hierarchy or the KP hierarchy is indicated by a bar graph like the SUM index 513. However, the expression of each frequency is not limited to these. Instead of a numerical value, specific icons may be used to express the frequency by arranging them by the number thereof, or the size of a specific figure may be used to express the same. In any case, it is sufficient that each frequency be integrally displayed and be able to be immediately understood. Further, the KP index 523 is not limited to the bar graph display mode and may be any display mode that is unified with the SUM index 513.

Further, in the example shown in FIG. 4A, the SUM index 513 is indicated as a bar graph in which the number of times that the result of the measurement falls under the KR hierarchy and the number of times that the result of the measurement falls under the KP hierarchy are summed up and integrated. However, in order to facilitate the understanding of the breakdown of the number of times, for example, a separator line may be added to the boundary part between each number of times. Further, when the KP hierarchy is further divided into a plurality of sections according to the degree of the walking abnormality, the determination unit 210a may determine which section the result of the measurement falls under, and display the KP hierarchy so that the frequency in each section can be understood. In this case, like the SUM index 513 shown in FIG. 4A, the KP index 523 shown in FIG. 4B may also be displayed so that the frequency in each section can be understood.

Figure 5:
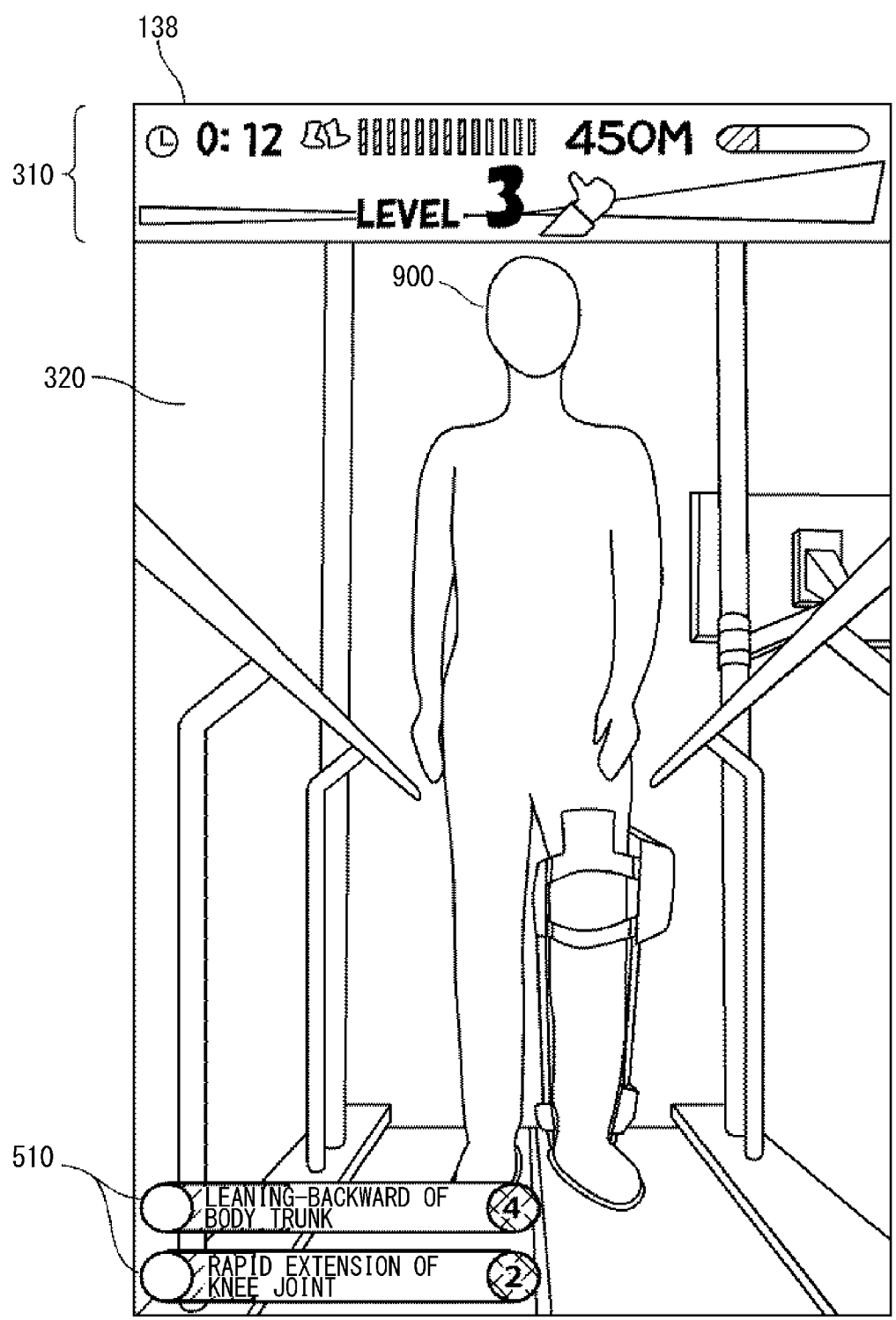
FIG. 5 is a diagram showing a display example of a training monitor during a training attempt.

FIG. 5 is a diagram showing a display example of the training monitor 138 during a training attempt. A status area 310 is provided at the top of the training monitor 138 and status information for the training attempt is displayed in the status area 310. The status information includes an attempt duration, a walking distance, a training level, a score indicator, and the like. The attempt duration is a time from the start of the attempt, and the duration is measured by a timer (not shown). The walking distance is measured from the integrated amount in which the treadmill drive unit 211 has rotated the belt 132. The training level indicates the degree of difficulty of a training attempt and is updated each time the trainee 900 satisfies a criterion set in advance. The score indicator is increased or reduced in accordance with addition or subtraction of the acquired points.

A camera image 320 is projected on an area other than the status area 310 of the training monitor 138. The camera image 320 is a whole-body image of the trainee 900 taken by the front camera unit 140 or the side camera unit 141, and is displayed as a real-time video image of, for example, 60 fps. The trainee 900 can check his/her own figure during a training attempt as a real-time video image. Note that the trainee 900 faces the training monitor 138, and accordingly the camera image 320 may be subjected to a mirror-image inversion in terms of visibility as shown in FIG. 5 when the image taken by the front camera unit 140 is displayed. These display video images are shaped by the display shaping unit 210b and are supplied from the display control unit 213 to the training monitor 138 as video image signals.

The determination unit 210a sequentially determines whether the walking of the trainee 900 is abnormal during the progress of the training attempt as described above. When the determination unit 210a determines any abnormal walking symptoms, the display shaping unit 210b shapes the first object 510 or the second object 520 according to the abnormal walking symptom, and displays the shaped first object 510 or the shaped second object 520 on the peripheral part of the camera image 320. In the example shown in FIG. 5, "leaning-backward of the body trunk" and "excessive bending of the knee joint" are determined as the specific abnormal walking symptoms, and the two first objects 510 are displayed. Each of the KR index 512 and the SUM index 513 of the first objects 510 indicates the frequency at the time of the respective determinations.

During a training attempt, the first object 510 and the second object 520 are displayed only in a predetermined peripheral area (the lower left area in the example in FIG. 5) since it is not preferred that the objects largely block the trainee 900 from being viewed in the camera image 320. Further, the display time for displaying each object is kept to about several seconds after the determination. That is, during the progress of a training attempt, the display is updated so that some of the determined abnormal walking symptoms are displayed in accordance with the progress of the training attempt rather than all of the determined abnormal walking symptoms being displayed one after another.

As a display method for displaying objects sequentially generated in a limited area, for example, an old object may be overwritten each time a new object is generated. In addition, the first object 510 indicating the specific abnormal walking symptom may be preferentially displayed, for example, by increasing the display time or by overwriting the second object 520 newer than the old first object 510. The size and the color of the first object 510 may differ from those of the second object 520, or animation may be used in accordance with the timing of displaying or deleting.

Figure 6:
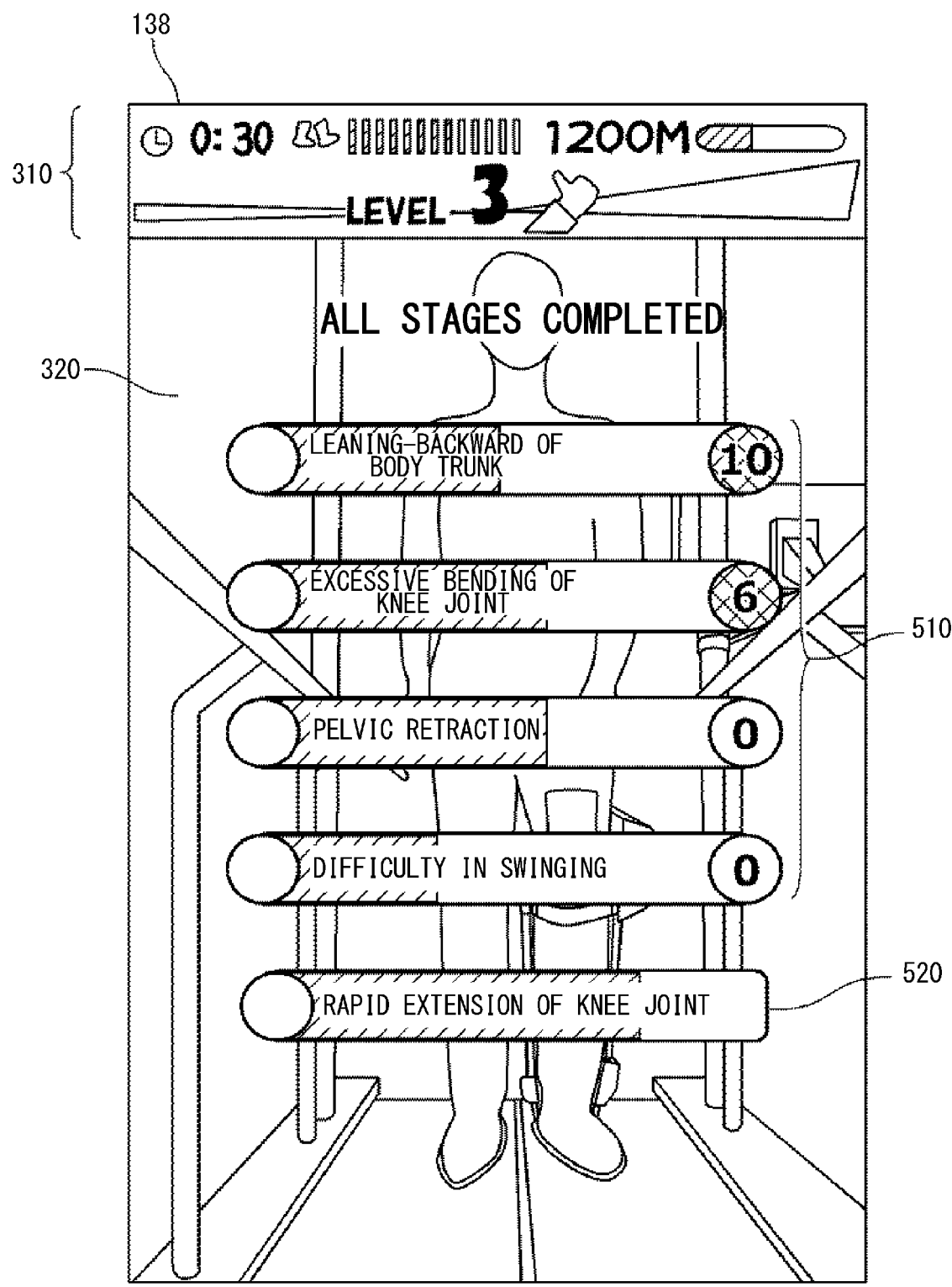
FIG. 6 is a diagram showing a display example of the training monitor after a training attempt.

FIG. 6 is a diagram showing a display example of the training monitor 138 after a training attempt. At the timing when a training attempt ends, all abnormal walking symptoms detected throughout the training attempt are displayed. In the example shown in FIG. 6, the four first objects 510 ("leaning-backward of the body trunk", "excessive bending of the knee joint", "pelvic retraction", "difficulty in swinging" as the specific abnormal walking symptoms) and the one second object 520 ("rapid extension of the knee joint" as the specific abnormal walking symptom) are displayed.

At this stage, considering the fact that the trainee 900 wants to fully recognize the result of the determination as a review of the training attempt, the objects are each displayed relatively large one after another in the center of the camera image 320. In this case, all objects corresponding to the detected abnormal walking symptoms may be displayed at once. If all the objects cannot be displayed at once due to an insufficient the display area, they may be displayed while the objects are sequentially switched by using, for example, a scroll display method. Note that in the display after the training attempt, the first object 510 may be displayed preferentially over the second object 520. For example, as shown in FIG. 6, the first objects 510 are displayed above the second object 520.

Figure 7:
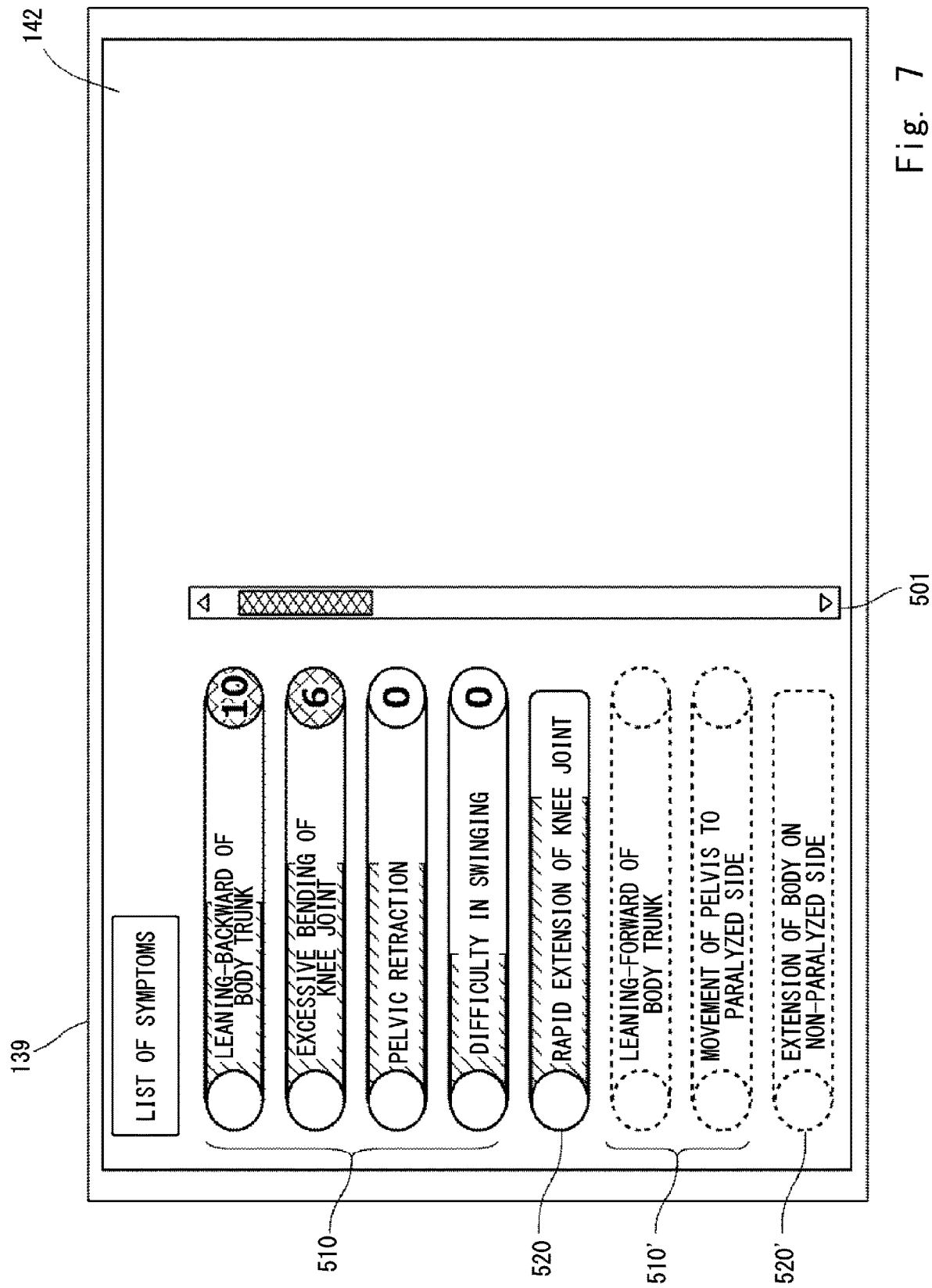
FIG. 7 is a diagram showing a display example of a management monitor after a training attempt.

FIG. 7 is a diagram showing a display example of the management monitor 139 after a training attempt. The abnormal walking symptoms detected throughout the training attempt are also displayed on the management monitor 139. While the display on the training monitor 138 is a graphical display with high visibility since it is for the trainee 900, the display on the management monitor 139, which is a display for the operator 910 assisting a training, is a display that puts emphasis on an accurate conveyance of information.

In this embodiment, the detected abnormal walking symptoms are displayed as the first object 510 and the second object 520, and the undetected abnormal walking symptoms are displayed as a first object 510' and a second object 520'. The color of the first and the second objects 510' and 520' is, for example, entirely light gray, and they are displayed below the first and the second objects 510 and 520. Note that all objects may be displayed in one screen, but if there are objects that cannot be displayed at the lower part of the screen as shown in FIG. 7, a scroll bar 501 may be displayed to receive a flick operation or the like from the operator 910. When the touch panel 142 receives a flick operation performed by the operator 910, the display shaping unit 210b scrolls the displayed object in the operation direction and makes the hidden objects displayed.

In this embodiment, the objects displayed on the management monitor 139 and the objects displayed on the training monitor 138 have the same display mode, the object displayed on the management monitor 139, however, may have a more detailed display mode. Note that even in such a case, the objects displaying the result of the determination of the specific abnormal walking symptom may be integrally displayed, for example, in such a manner that the frequency in which the result of the measurement falls under the KR hierarchy and the total frequency in which the result of the measurement falls under either the KR hierarchy or the KP hierarchy are juxtaposed.

When the object displayed on the management monitor 139 is selected by a tap operation performed by the operator 910, advice about an adjustment item for improving the abnormal walking symptom according to the selected object appears. This advice display function will be specifically described.

Figure 8:
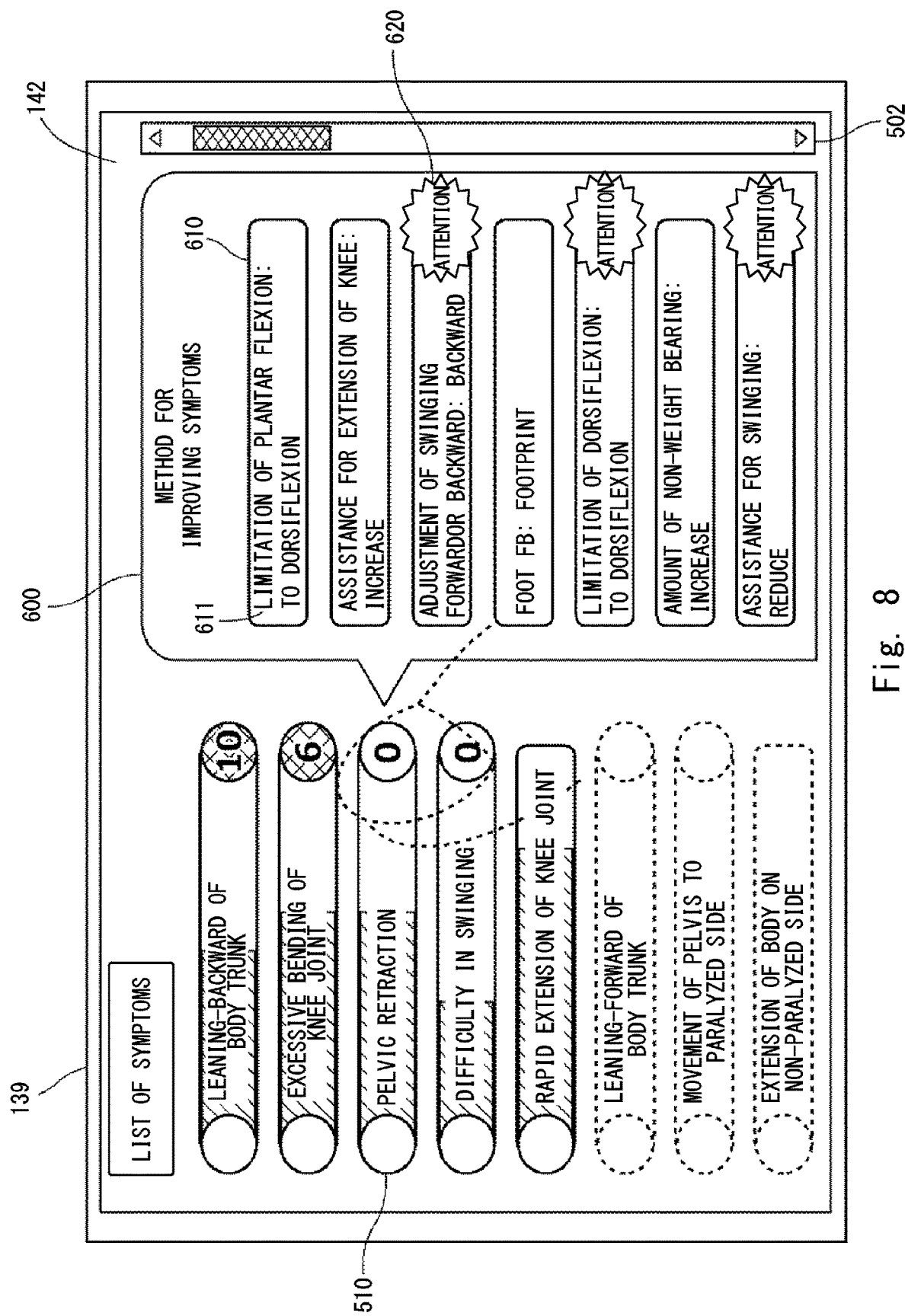
FIG. 8 is a diagram showing a display example in which the management monitor displays methods for improving the symptoms.

FIG. 8 is a diagram showing a display example that displays advice for improving the symptom on the management monitor 139. As shown in FIG. 8, for example, when the first object 510 indicating the specific abnormal walking symptom of "pelvic retraction" is tapped, a list of pieces of advice for improving the symptom of "pelvic retraction" is displayed as a method for improving the symptom. Specifically, an advice window 600 is displayed in such a manner that it protrudes from the selected first object 510 indicating "pelvic retraction", and each piece of advice corresponding to "pelvic retraction" is arranged as a third object 610 in the advice window 600.

The third object 610 includes an advice title 611 representing the advice as character information, for example, "Limitation of plantar flexion: To dorsiflexion". It should be noted that the advice for improving the symptoms indicates, concerning a plurality of adjustment items prepared in the walking training apparatus 100, which and how items should be adjusted to effectively improve the abnormal walking symptoms of the trainee 900. If the advice indicates "Limitation of plantar flexion: To dorsiflexion", for the adjustment of the adjustment mechanism 126 provided between the lower leg frame 123 and the sole frame 124 in the walking assistance apparatus 120, changing the limitation of the rotation range on the plantar-flexion side to the dorsiflexion side is likely to improve the symptom.

As shown in FIG. 8, as the advice for improving the symptoms of "pelvic retraction", in addition to "Limitation of plantar flexion: To dorsiflexion", "Assistance for extension of the knee: Increase", "Adjustment of swinging forward or backward: Backward", "Foot FB: Footprint", "Limitation of dorsiflexion: To dorsiflexion", "Amount of non-weight bearing: Increase", and "Assistance for swinging: Reduce" are displayed as the third objects 610 in the advice window 600. If there are any third objects 610 that cannot be displayed, a scroll bar 502 may be displayed to receive a flick operation or the like.

Note that the advice displayed in this example is not limited to the advice about the mechanical and physical adjustment of the adjustment mechanism prepared in the walking training apparatus 100. For example, "Foot FB: Footprint" indicates that a footprint mark may be superimposed and displayed on a desired grounding point with respect to the foot of the trainee 900 in the camera image 320 during a training attempt. When such a footprint mark is displayed, the trainee 900 can use the footprint mark as an index for adjusting his/her gait.

As shown in FIG. 8, attention icons 620 are superimposed and displayed on the specific third objects 610. Specifically, the attention icons 620 are respectively superimposed on the third objects 610 each indicating "Adjustment of swinging forward or backward: Backward", "Limitation of dorsiflexion: To dorsiflexion", and "Assistance for swinging: Reduce". The attention icons 620 indicate that caution is required when these pieces of advice are adopted. The details thereof will be described later.

In the item table 217b, the pieces of advice are associated with the respective abnormal walking symptoms as a list. The display shaping unit 210b shapes the third object 610 with reference to the item table 217b for the advice for the selected abnormal walking symptom. However, the display shaping unit 210b does not display the corresponding third objects 610 in the advice window 600 in the order described in the item table 217b. In this embodiment, regarding advice for improving the selected abnormal walking symptom ("pelvic retraction" in FIG. 8), the display shaping unit 210b preferentially displays the advice that is common to advice for improving the abnormal walking symptoms ("leaning-backward of the body trunk", "excessive bending of the knee joint", "difficulty in swinging", and "rapid extension of the knee joint" in FIG. 8) in the results of other determinations in which the determination unit 210a determines the abnormal walking. In this way, the display order of the third objects 610 shown in FIG. 8 is determined.

The procedure for determining the display order is described below. FIG. 9 is a diagram showing a list of the detected abnormal walking symptoms in FIG. 8 and a method for improving the detected symptoms. The list shown in FIG. 9 corresponds to an excerpt of only the part related to the detected abnormal walking symptoms from the item table 217b. For example, eight pieces of advice ("Limitation of plantar flexion: To dorsiflexion", "Limitation of dorsiflexion: To dorsiflexion", "Amount of non-weight bearing: Increase", "Assistance for extension of the knee: Increase", "Assistance for swinging: Reduce", "Adjustment of swinging forward or backward: Backward", "Foot FB: Footprint", and "Non-weight-bearing position of the leg: Outside") about the improvement method are associated with the abnormal walking symptom of "pelvic retraction".

FIG. 10 is a diagram showing processing done until a display mode of the improvement method is determined and shows a result of analysis of each piece of advice associated with the selected abnormal walking symptom of "pelvic retraction". A first associated piece of advice is "Limitation of plantar flexion: To dorsiflexion", and referring to FIG. 9, it is seen that this piece of advice is common to the pieces of advice associated with the abnormal symptoms of "leaning-backward of the body trunk", "difficulty in swinging", and "rapid extension of the knee joint". Accordingly, the number of pieces of advice that overlap with the pieces of advice associated with other abnormal walking symptoms (hereinafter referred to as the number of overlaps) is "4", including the first piece of advice. A second piece of advice is "Limitation of dorsiflexion: To dorsiflexion", and this piece of advice is not common to those associated with other symptoms. Accordingly, the number of overlaps is "1", including the second piece of advice. Similarly, regarding a third piece of advice of "Amount of non-weight bearing: Increase", the number of overlaps is "1", including the third piece of advice. As a fourth piece of advice of "Assistance for extension of the knee: Increase" is common to the pieces of advice associated with the abnormal symptoms of "excessive bending of the knee joint" and "rapid extension of the knee joint", the number of overlaps is "3", including the fourth piece of advice. Counting in a way similar to the above way of counting, the number of overlaps of a fifth piece of advice of "Assistance for swinging: Reduce" is "1", including the fifth piece of advice, the number of overlaps of a sixth piece of advice of "Adjustment of swinging forward or backward: Backward", is "2", including the sixth piece of advice, the number of overlaps of a seventh piece of advice of "Foot FB: Footprint", is "2", including the seventh piece of advice, and the number of overlaps of an eighth piece of advice of "Non-weight-bearing position of the leg: Outside" is "1", including the eighth piece of advice.

Based on the above results of the analysis, the display order is set higher as the number of overlaps becomes larger. Specifically, "Limitation of plantar flexion: To dorsiflexion" having the largest number of overlaps is set to the display order of "1", and "Assistance for extension of the knee: Increase" having the next largest number of overlaps is set to the display order of "2". Regarding the same number of overlaps, giving the display order in the list order determines the display order from 1 to 8 as shown in FIG. 10. The display shaping unit 210b displays the third objects 610 generated for each advice piece in the advice window 600 from the top thereof according to the display order determined in this way. By displaying as described above, the operator 910 who is an assistant can appropriately and immediately recognize which and how adjustment items, which have a complicated relationship with each other, should be adjusted to effectively improve the abnormal walking symptom of the trainee 900.

In the above description, an example has been described in which the display order of the advice associated with the selected symptom that is common to the advice associated with other symptoms becomes higher as an example of a preferential display. However, an example of a preferential display is not limited to this, and the order may be directly displayed by numerical values, the advice window 600 may be made larger as the advice has a higher priority, or the display may be made to stand out using animation.

In FIG. 10, "conflict with other improvement methods" indicates the result of the analysis whether each piece of advice associated with the symptom of "pelvic retraction" conflicts with pieces of advice associated with other detected symptoms. For example, referring to FIG. 9, it is seen that the second piece of advice "Limitation of dorsiflexion: To dorsiflexion" conflicts with "Limitation of dorsiflexion: To plantar flexion", which is a piece of advice associated with "excessive bending of the knee joint". That is, for the same adjustment items, opposing (i.e., conflicting) adjustments are instructed. In such a case, there is a possibility that one symptom may be improved but the other symptom may be not improved or made worse, and accordingly care should be taken when adopting this piece of advice. As described above, if there is a conflict of the advice associated with the selected symptom with the advice associated with another symptom, "Yes" is indicated, and if there is no conflict, "No" is indicated.

The display shaping unit 210b superimposes and displays the attention icon 620 on the third object 610 corresponding to the advice in which "Yes" is described in the column of "conflict with other improvement methods" as shown in FIG. 8. The operator 910 who is an assistant can determine which adjustment item to adjust after he/she checks this attention icon, so that he/she can avoid making the specific abnormal walking symptom worse without himself/herself being aware of it.

Figure 11:
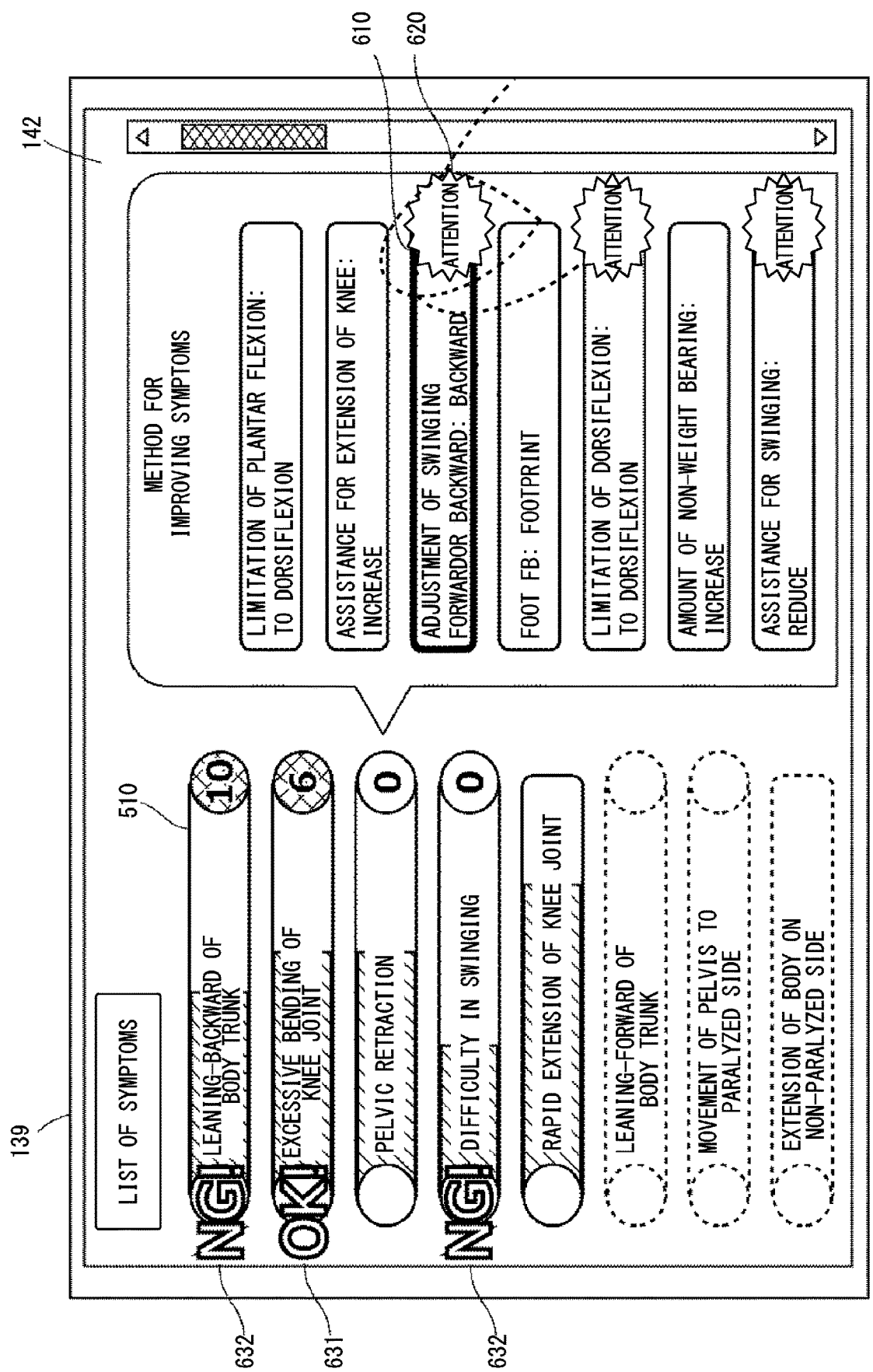
FIG. 11 is a diagram showing a display example of the abnormal walking symptoms related to a selected improvement method.

When the operator 910 taps the third object 610 on which the attention icon 620 is superimposed, the display mode of the first and the second objects 510 and 520 of the abnormal walking symptom among the detected abnormal walking symptoms with which the same advice as the advice corresponding to the third object 610 is associated is changed. Further, the display mode of the first and the second objects 510 and 520 of the abnormal walking symptom among the detected abnormal walking symptoms with which the advice that conflicts with the advice corresponding to the third object 610 is associated is changed to a display mode different from that of the first and the second objects 510 and 520 associated with the same advice as the advice corresponding to the third object 610. FIG. 11 is a diagram showing a display example of the abnormal walking symptom displayed in the display mode changed in such a manner.

FIG. 11 is a display example of a case in which the operator 910 taps the third object 610 indicating "Adjustment of swinging forward or backward: Backward" on which the attention icon 620 is superimposed in the display state shown in FIG. 8. It can be seen from FIG. 9 that the advice of "Adjustment of swinging forward or backward: Backward" is also included as the advice associated with the abnormal walking symptom of "excessive bending of the knee joint". Therefore, the display shaping unit 210b superimposes a first attribute icon 631 showing "OK" on the peripheral part of the first object 510 indicating the abnormal walking symptom of "excessive bending of the knee joint". By checking the first attribute icon 631, the operator 910 can recognize that, when the advice of "Adjustment of swinging forward or backward: Backward" is adopted, the abnormal walking symptom of "excessive bending of the knee joint" can be improved simultaneously.

Meanwhile, it can be seen from FIG. 9 that the abnormal walking symptoms of "leaning-backward of the body trunk" and "difficulty in swinging" include the advice of "Adjustment of swinging forward or backward: Forward". As the advice of "Adjustment of swinging forward or backward: Forward" conflicts with the advice of "Adjustment of swinging forward or backward: Backward", the display shaping unit 210b superimposes a second attribute icon 632 showing "NG" on the peripheral part of each of the first objects 510 each indicating the abnormal walking symptoms of "leaning-backward of the body trunk" and "difficulty in swinging". By checking the second attribute icon 632, the operator 910 can recognize that, when the advice of "Adjustment of swinging forward or backward: Backward" is adopted, it may not contribute to the improvement of the abnormal walking symptom of "leaning-backward of the body trunk" and "difficulty in swinging" or may make the symptoms worse. That is, the operator 910 can comprehensively determine whether to adopt the advice by checking the abnormal walking symptom on which the first and the second attribute icons 631 and 632 are superimposed.

In the above example, the case where the third object 610 on which the attention icon 620 is superimposed is tapped has been described. However, the first attribute icon 631 may be similarly superimposed even in the case where the third object 610 on which the attention icon 620 is not superimposed is tapped. That is, the first attribute icon 631 may be superimposed on the peripheral part of the first object 510 or the second object 520 indicating the abnormal walking symptom including the same advice as the advice indicated by the third object 610.

Further, in the above example, an example in which the first attribute icon 631 or the second attribute icon 632 is superimposed as one of the changes in the display mode of the first object 510 and the second object 520 has been described, but the change in the display mode is not limited to this. For example, the color of the object itself may be changed to a bluish color to be highlighted when the same advice as that associated with other symptoms is included, and the color of the object itself may be changed to a reddish color to be highlighted when the conflicting advice is included. Scaling and a display effect using animation may be employed.

Figure 12:
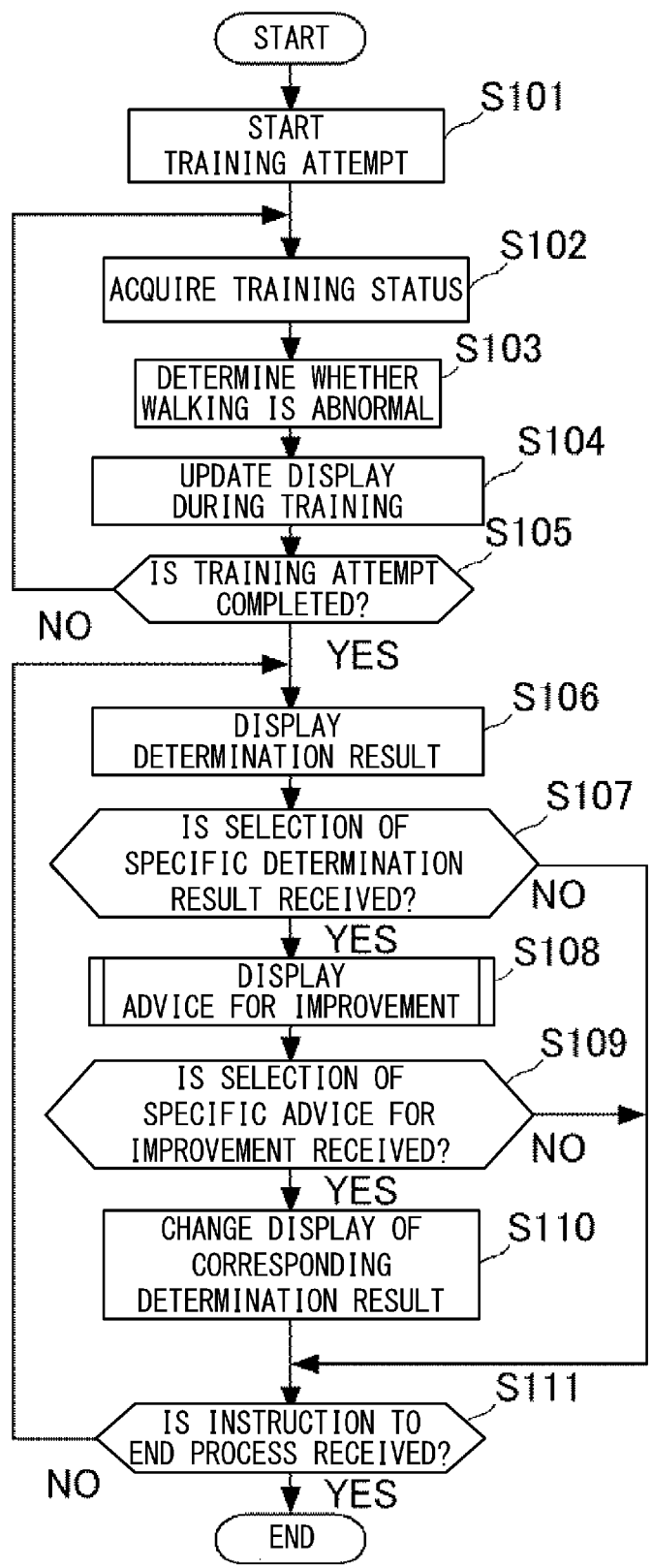
FIG. 12 is a flowchart showing a processing flow in a series of training attempts.

Next, control processing for a series of training attempts is described. FIG. 12 is a flowchart showing a processing flow in a series of training attempts. In Step S101, the overall control unit 210 starts a training attempt according to the training menu specified by the operator 910 or the trainee 900. In Step S102, when the training attempt is started, the overall control unit 210 acquires the training status. Specifically, the overall control unit 210 causes the image processing unit 216 to capture image-pickup images taken by the front camera unit 141 and the side camera unit 142, perform image processing, and perform analysis processing for analyzing a gait. Further, the overall control unit 210 acquires an output signal from the load sensor 222 or the like. In Step S103, the determination unit 210a determines whether the walking of the trainee 900 is an abnormal walking using the training status acquired in Step S102. Specifically, as described above, the determination unit 210a determines whether the walking of the trainee 900 corresponds to any of the plurality of abnormal walking symptoms set in advance. In particular, for a specific abnormal walking symptom, the determination unit 210a also determines whether the result of measurement of the measurement target is included in the KP hierarchy or the KR hierarchy.

In Step S104, the display shaping unit 210b updates the displays on the training monitor 138 and the management monitor 139 via the display control unit 213. Specifically, regarding the training monitor 138, the display shaping unit 210b updates the status area 310 in accordance with the progress of the training attempt, and updates the camera image 320 in accordance with the output of the front camera unit 140 or the side camera unit 141. In particular, when the abnormal walking is determined in Step S103, the display shaping unit 210b shapes the first object 510 or the second object 520 according to the detected abnormal walking symptoms and displays the shaped object on the peripheral part of the camera image 320 as described with reference to FIG. 5. Regarding the management monitor 139, in addition to the update similar to that performed in the training monitor 138, more detailed information about abnormal walking symptoms may be displayed.

In Step S105, the overall control unit 210 determines whether the scheduled training attempt has been completed. If the overall control unit 210 determines that the training attempt has not been completed, the process returns to Step S102. If the overall control unit 210 determines that the training attempt has been completed, the process proceeds to Step S106.

In Step S106, the display shaping unit 210b summarizes the results of the determination of the abnormal walking symptoms determined by the determination unit 210a during the training attempt, and displays it in the mode shown in FIG. 6 on the training monitor 138 and in the mode shown in FIG. 7 on the management monitor 139.

In Step S107, the operation reception unit 212 receives an operation of the touch panel 142 performed by the operator 910. The overall control unit 210 acquires a reception signal from the operation reception unit 212 and determines whether either first object 510 or the second object 520, which is the result of the determination displayed on the management monitor 139, has been selected. If the overall control unit 210 determines that the selection has been made, the process proceeds to Step S108. If the overall control unit 210 determines that the selection has not been made, the process skips to Step S111.

Figure 13:
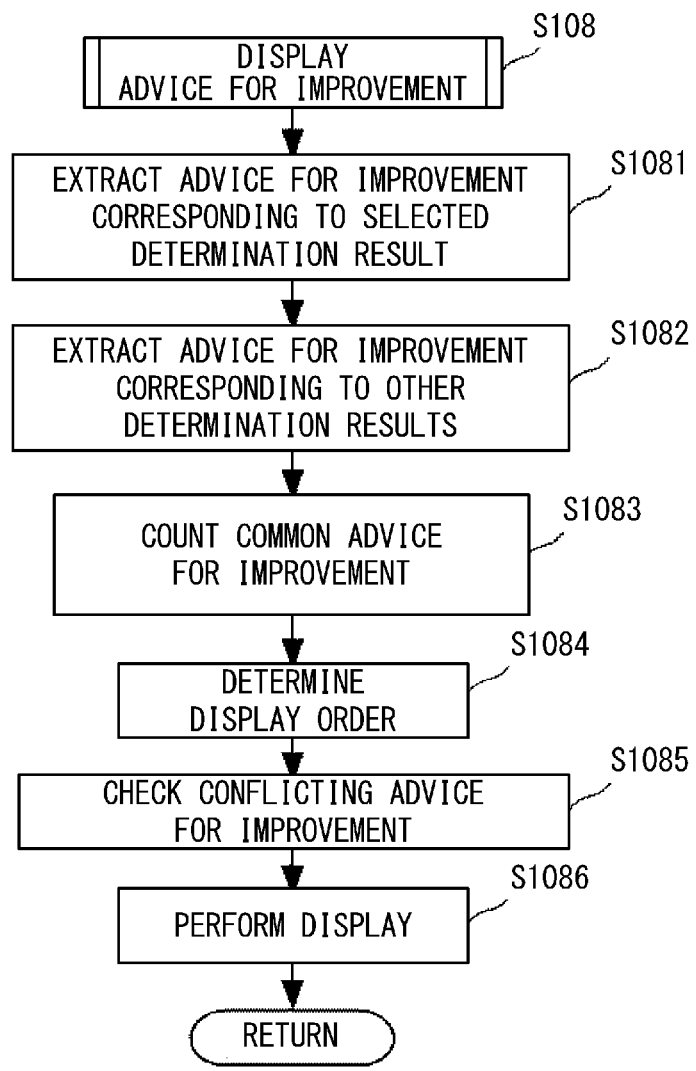
FIG. 13 is a flowchart showing a processing flow regarding a display of advice for improvement.

In Step S108, the display shaping unit 210b displays advice for improving the abnormal walking symptom according to the selected object. FIG. 13 is a flowchart showing a processing flow regarding a display of advice for improvement in Step S108. In Step S1081, the display shaping unit 210b extracts pieces of advice associated with the abnormal walking symptom according to the selected object. Next, in Step S1082, the display shaping unit 210b extracts, from the item table 217b, pieces of advice that are associated with other abnormal walking symptoms determined during the training attempt.

In Steps S1083, the display shaping unit 210b determines whether each of the pieces of advices associated with the abnormal walking symptoms according to the selected object are common to the pieces of advice extracted in Step S1082, and counts the number of overlaps as described with reference to FIG. 10. Next, in Step S1084, the display order is determined in accordance with the number of overlaps. In Step S1085, the display shaping unit 210b checks whether there are any pieces of advice which conflict with the pieces of advice associated with the abnormal walking symptoms according to the selected object in the pieces of advice extracted in Step S1082. Upon completion of these processes, the process proceeds to Step S1086, and the display shaping unit 210b displays the pieces of advice for improving the abnormal walking symptom according to the selected object in the mode shown in FIG. 8.

With reference to FIG. 12, the explanation is continued. In Step S109, the operation reception unit 212 receives an operation of the touch panel 142 performed by the operator 910. The overall control unit 210 acquires a reception signal from the operation reception unit 212 and determines whether any of the third objects 610 displayed on the management monitor 139 has been selected. If the overall control unit 210 determines that the selection has been made, the process proceeds to Step S110. If the overall control unit 210 determines that the selection has not been made, the process skips to Step S111.

In Step S110, as shown in FIG. 11, the display shaping unit 210b superimposes the first attribute icon 631 showing "OK" on the first object 510 and the second object 520 of the abnormal walking symptom associated with the same advice as the advice according to the selected third object 610. Further, the display shaping unit 210b superimposes the second attribute icon 632 showing "NG" on the first object 510 and the second object 520 of the abnormal walking symptom associated with the advice that conflicts with the advice according to the selected third object 610.

In Step S111, the overall control unit 210 checks whether an instruction to end the process has been received from the trainee 900 or the operator 910. If the overall control unit 210 has not received the instruction, the process returns to Step S106. If the overall control unit 210 has received the instruction, it ends the series of processes.

In this embodiment described above, the example has been described in which the selection of one first object 510 or one second object 520 is received, and regarding the advice for improving the abnormal walking symptom, the advice that is common to that for other abnormal walking symptoms is preferentially displayed. However, the present disclosure is not limited to this, and a function may be added in which selections of a plurality of objects are received and regarding the common advice for improving these abnormal walking symptoms, the advice common to that for other abnormal walking symptoms is preferentially displayed. Further, if such a display mode is supported, the operator 910 can appropriately adjust the adjustment items when it is desired to improve a plurality of abnormal walking symptoms simultaneously.

Further, the pieces of advice may include those greatly contribute to the improvement of the abnormal walking symptoms and those that do not, and therefore a degree of importance may be set for each pieces of advice, and the order of priority may be changed in consideration of the degree of importance. For example, the degree of importance of "Assistance for extension of the knee: Increase" in which a pulling force acts on the trainee 900 may be set higher than that of the "Foot FB: Footprint" which is only displayed on the training monitor 138. Alternatively, the display format may be changed according to the degree of importance, instead of reflecting the order of priority. For example, the advice having a high degree of importance is made to be displayed larger. As described above, if a degree of importance is set for each advice and the display mode is changed, the operator 910 can easily adopt more effective advice.

Further, the order of priority of each advice piece may be changed in consideration of the past display history. For example, the order of priority for advice that has been displayed several times for the previous training attempts is lowered. The past display history is recorded in the trainee information DB 217a that is updated every time a training attempt is performed. Alternatively, the display format may be changed according to the past display history, instead of according to the order of priority. For example, the advice that has been frequently displayed is made to be displayed less prominently. As described above, if the display history is recorded for each advice piece and the display mode is changed according to the display history, the operator 910 can easily adopt more effective advice.

Figure 14:
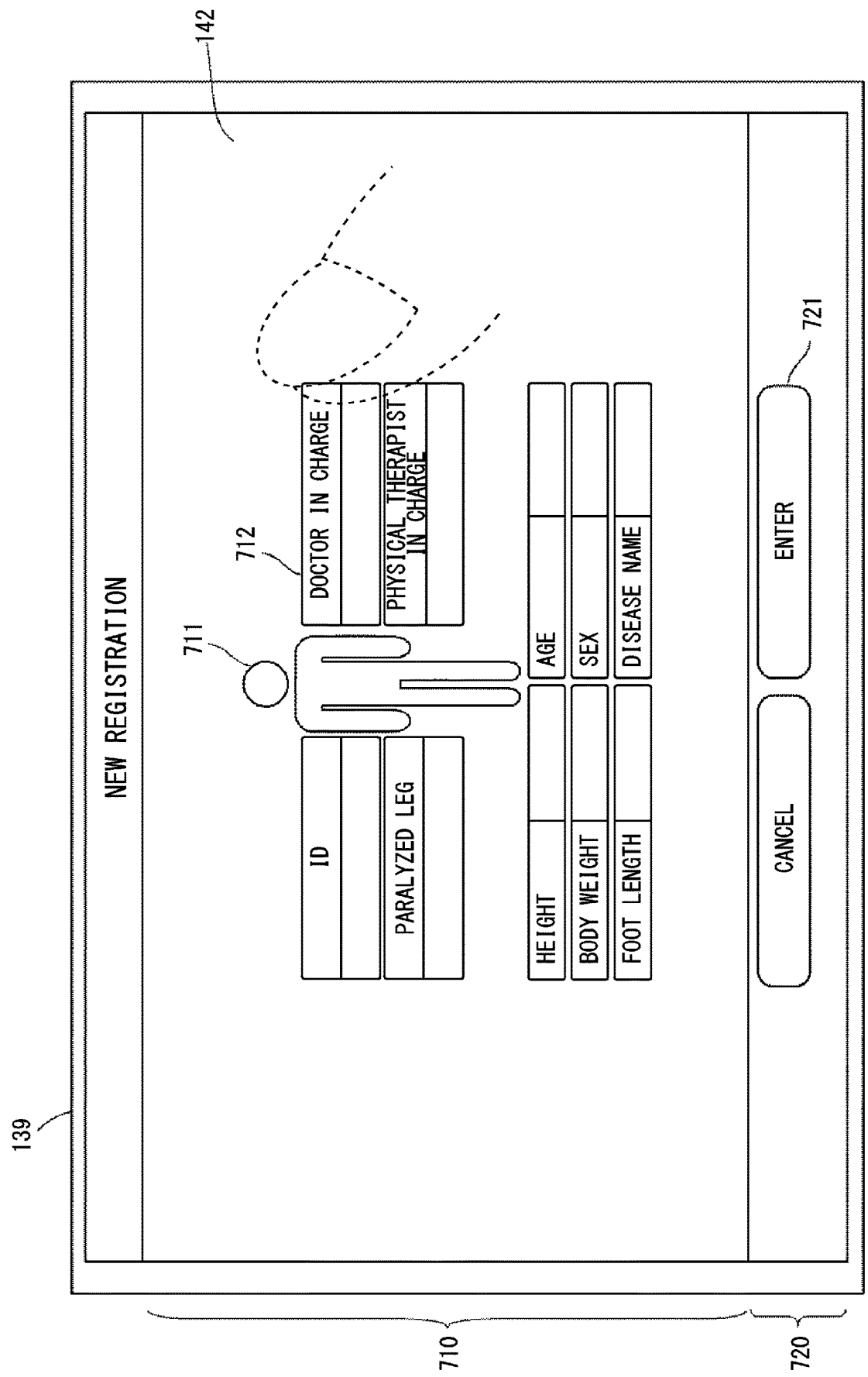
FIG. 14 is a diagram showing a display example of an input screen including character input items.

Next, a user interface for inputting characters on the management monitor 139 is described. FIG. 14 is a diagram showing a display example of an input screen including character entry items. An entry screen shown in FIG. 14 is a new registration screen for a trainee and is a display example before a character input is required. The new registration screen includes a first frame 710 and a second frame 720. The first frame 710 includes graphics 711 indicating a humanoid and various input windows 712. The second frame 720 includes two operation buttons 721: one is "enter" that determines the input and the other is "cancel" that cancels the input. In such a display state, when the operator 910 taps, for example, the input window 712 of "doctor in charge", the display screen changes to a character reception state for receiving the name of the doctor in charge.

Figure 15:
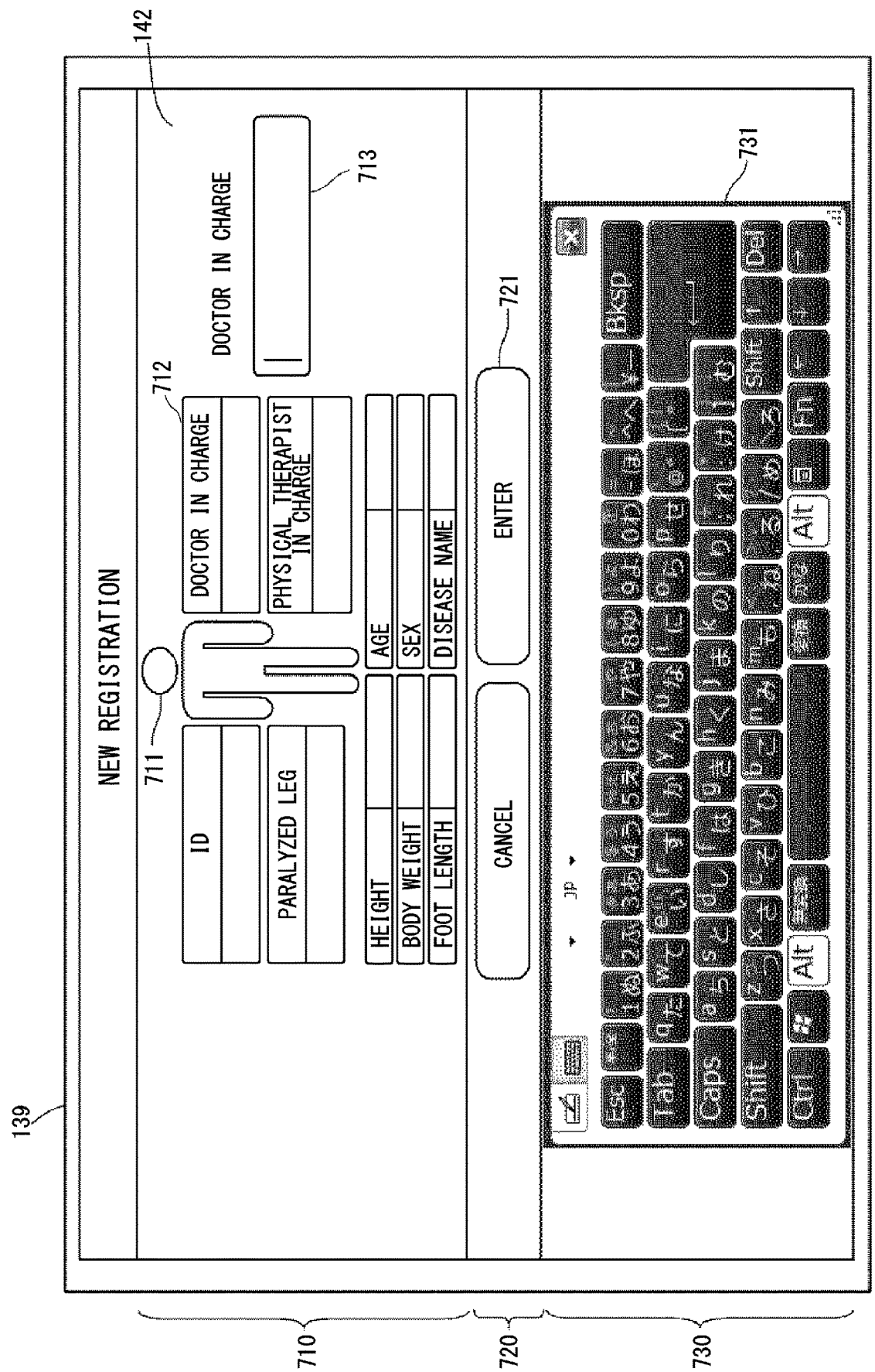
FIG. 15 is a diagram showing a display example of a character reception state in which a character input is received.

FIG. 15 is a diagram showing a display example of a character reception state in which a character input is received. As shown in FIG. 15, the first and the second frames 710 and 720 have a reduced vertical width and slide upward in the screen. Then, a third frame 730 is provided in the generated surplus area.

The graphics 711 and the input window 712 included in the first frame 710 are both reduced in the vertical direction as the vertical width of the first frame 710 is reduced. Further, most of the upper and lower margins of the first frame 710 that has existed before the change to the character reception state are removed. Meanwhile, a text window 713 newly appears for "doctor in charge", which is a target of a character input.

As the two operation buttons 721 included in the second frame 720 are operated even in the character reception state, they are not reduced in the vertical direction and maintain their shapes. However, most of the upper and lower margins of the second frame 720 that has existed before the change to the character reception state are removed.

In the third frame 730, a soft keyboard 731 is displayed. The operator 910 can perform a character input by tapping each key of the soft keyboard 731. When the character input is completed, the operation button 721 of "enter" is tapped to determine the input. By adopting such a user interface for a character input, the operator 910 can correctly recognize necessary information and can perform a character input more easily.

As described above, although the walking training apparatus 100 has been described as an example of a walking training system, the walking training system does not necessarily have a configuration in which all functional elements are integrated in the walking training apparatus 100. For example, at least one of the functions of the determination unit 210a and the display shaping unit 210b for determining an abnormal walking may be performed by a calculation unit provided in a server connected to the walking training apparatus 100 via a network. In this case, the server transmits the determined result and the shaped display video image data to the walking training apparatus 100. The overall control unit 210 of the walking training apparatus 100 achieves a display similar to that of the above-described embodiment using the transmitted result of the determination and display video image data. Thus, the walking training system may be configured to include the server and the walking training apparatus 100.

The program(s) can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g., magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program(s) may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A walking training system, comprising:
a treadmill that urges a trainee to walk;
a determination unit configured to determine whether a walking of the trainee who walks on the treadmill is an abnormal walking based on a plurality of predetermined abnormal walking symptoms;
a display unit configured to display a result of a determination of each of the plurality of abnormal walking symptoms by the determination unit;
a reception unit configured receive a selection of at least one result of the determination from the results of the determinations, each of which is displayed on the display unit, wherein
regarding pieces of advice about adjustment items for improving the abnormal walking symptoms in the result of the determination which the reception unit has received the selection, the display unit preferentially displays the pieces of advice that are common to pieces of advice about adjustment items for improving the abnormal walking symptoms in a result of another determination in which the determination unit determines the abnormal walking.

2. The walking training system according to claim 1, wherein the display unit changes a display mode of each of the pieces of advice while taking a past display history into consideration.

3. The walking training system according to claim 1, wherein the display unit changes a display mode of each of the pieces of advice based on a degree of importance set in advance for each adjustment item.

4. The walking training system according to claim 1, wherein
the reception unit receives a selection of at least one piece of advice from the pieces of advice, each of which is displayed on the display unit, and
a display mode changes the display mode of the result of the determination corresponding to the abnormal walking symptom with which the same piece of advice as the piece of advice received by the reception unit is associated.

5. The walking training system according to claim 1, wherein
the reception unit receives a selection of at least one piece of advice from the pieces of advice, each of which is displayed on the display unit, and
a display mode changes the display mode of the result of the determination corresponding to the abnormal walking symptom with which a piece of advice that conflicts with the piece of advice received by the reception unit is associated.

6. A display method for displaying, on a display unit, pieces of advice about a walking determined to be an abnormal walking in a walking training system including a treadmill that urges a trainee to walk and the display unit, the display method comprising:
- a determination step of determining whether a walking of the trainee who walks on the treadmill is an abnormal walking based on a plurality of predetermined abnormal walking symptoms;
- a first display step of displaying, on the display unit, a result of a determination of each of the plurality of abnormal walking symptoms by the determination step;
- a reception step of receiving a selection of at least one result of the determination from the results of the determinations, each of which is displayed on the display unit; and
- a second display step of displaying pieces of advice about adjustment items for improving the abnormal walking symptoms in the result of the determination which the selection has received in the reception step, wherein
  - in the second display step, the pieces of advice that are common to pieces of advice about adjustment items for improving the abnormal walking symptoms in a result of another determination in which the abnormal walking is determined are preferentially displayed.

7. A non-transitory computer readable medium storing a display program for displaying, on a display unit, pieces of advice about a walking determined to be an abnormal walking in a walking training system including a treadmill that urges a trainee to walk and the display unit, the display program causing a computer to execute:
- a determination step of determining whether a walking of the trainee who walks on the treadmill is an abnormal walking based on a plurality of predetermined abnormal walking symptoms;
- a first display step of displaying, on the display unit, a result of a determination of each of the plurality of abnormal walking symptoms by the determination step;
- a reception step of receiving a selection of at least one result of the determination from the results of the determinations, each of which is displayed on the display unit; and
- a second display step of displaying pieces of advice about adjustment items for improving the abnormal walking symptoms in the result of the determination which the selection has received in the reception step, wherein
- in the second display step, the pieces of advice that are common to pieces of advice about adjustment items for improving the abnormal walking symptoms in a result of another determination in which the abnormal walking is determined are preferentially displayed.

* * * * *